(12) United States Patent
Mohamed et al.

(10) Patent No.: US 9,901,337 B1
(45) Date of Patent: Feb. 27, 2018

(54) SUTURE STITCHES FOR CONTINUOUS SURGICAL SUTURING

(71) Applicant: iSuturing, LLC, Raleigh, NC (US)

(72) Inventors: Adel W. Mohamed, Raleigh, NC (US); Mansour H. Mohamed, Raleigh, NC (US); Dmitri D. Mungalov, Cary, NC (US)

(73) Assignee: iSuturing, LLC, Raleigh, NC (US)

( * ) Notice: Subject to any disclaimer, the term of this patent is extended or adjusted under 35 U.S.C. 154(b) by 0 days.

(21) Appl. No.: 15/710,099

(22) Filed: Sep. 20, 2017

Related U.S. Application Data

(60) Continuation of application No. 14/966,690, filed on Dec. 11, 2015, now Pat. No. 9,770,239, which is a continuation of application No. 13/898,103, filed on May 20, 2013, now Pat. No. 9,220,498, which is a division of application No. 13/012,965, filed on Jan. 25, 2011, now Pat. No. 8,465,504.

(51) Int. Cl.
*A61B 17/04* (2006.01)
*A61B 17/12* (2006.01)
*A61B 17/06* (2006.01)

(52) U.S. Cl.
CPC ...... *A61B 17/0469* (2013.01); *A61B 17/0491* (2013.01); *A61B 17/06* (2013.01); *A61B 17/06166* (2013.01); *A61B 2017/0498* (2013.01); *A61B 2017/061* (2013.01); *A61B 2017/06076* (2013.01)

(58) Field of Classification Search
CPC ............ A61B 17/0469; A61B 17/0491; A61B 2017/0498; A61B 2017/06076
USPC ......................................................... 606/144
See application file for complete search history.

(56) References Cited

U.S. PATENT DOCUMENTS

| | | | |
|---|---|---|---|
| 67,545 A | 8/1867 | Hodgins |
| 196,226 A | 10/1877 | Havell |
| 242,602 A | 6/1881 | Clough |
| 349,791 A | 9/1886 | Gibbonsy |
| 919,138 A | 4/1909 | Drake et al. |
| 1,583,271 A | 5/1926 | Biro |
| 2,327,353 A | 8/1943 | Karle |
| 2,959,172 A | 11/1960 | Held |
| 3,037,619 A | 6/1962 | Ernest |
| 4,204,541 A | 5/1980 | Kapitanov |
| 4,440,171 A | 4/1984 | Nomoto et al. |
| 4,465,070 A | 8/1984 | Eguchi |
| 4,524,771 A | 6/1985 | McGregor et al. |
| 4,641,652 A | 2/1987 | Hutterer et al. |
| 4,969,892 A | 11/1990 | Burton et al. |
| 5,152,769 A | 10/1992 | Baber |
| 5,356,424 A | 10/1994 | Buzerak et al. |
| 5,499,991 A | 3/1996 | Garman et al. |

(Continued)

*Primary Examiner* — Melanie Tyson
(74) *Attorney, Agent, or Firm* — Neo IP

(57) ABSTRACT

A device for making continuous suture stitches including a handle and a device head. The handle including a power source for the device head and a means for attachment to the device head. The device head including a suture thread supply; a needle rotationally movable, operable for moving the thread through a tissue; a hook operable for hooking and lifting the thread in automatic coordination with the needle; and a catcher operable for moving the thread into and out of the hook in automatic coordination with the hook; thereby providing a device for making continuous suture stitches for adjoining a first edge and a second edge of a tissue in an edge-to-edge interface.

20 Claims, 23 Drawing Sheets

(56) References Cited

U.S. PATENT DOCUMENTS

| | | |
|---|---|---|
| 5,507,743 A | 4/1996 | Edwards et al. |
| 5,520,703 A | 5/1996 | Essig et al. |
| 5,562,685 A | 10/1996 | Mollenauer et al. |
| 5,709,692 A | 1/1998 | Mollenauer et al. |
| 5,810,851 A | 9/1998 | Yoon |
| 5,911,689 A | 6/1999 | Smith et al. |
| 5,935,138 A | 8/1999 | William et al. |
| 5,947,983 A | 9/1999 | Solar et al. |
| 6,113,610 A | 9/2000 | Poncet |
| 6,520,973 B1 | 2/2003 | McGarry |
| 6,537,248 B2 | 3/2003 | Mulier et al. |
| 6,562,052 B2 | 5/2003 | Nobles et al. |
| 6,613,058 B1 | 9/2003 | Goldin |
| 6,626,917 B1 | 9/2003 | Craig |
| 6,663,633 B1 | 12/2003 | Pierson |
| 6,723,107 B1 | 4/2004 | Skiba et al. |
| 6,911,003 B2 | 6/2005 | Anderson et al. |
| 6,911,019 B2 | 6/2005 | Mulier et al. |
| 6,911,037 B2 | 6/2005 | Gainor et al. |
| 6,923,807 B2 | 8/2005 | Ryan et al. |
| 6,986,776 B2 | 1/2006 | Craig |
| 7,070,556 B2 | 7/2006 | Anderson et al. |
| 7,144,401 B2 | 12/2006 | Yamamoto et al. |
| D543,626 S | 5/2007 | Watschke et al. |
| 7,235,087 B2 | 6/2007 | Modesitt et al. |
| 7,269,324 B2 | 9/2007 | Crownover |
| 7,288,105 B2 | 10/2007 | Oman et al. |
| 7,290,494 B2 | 11/2007 | Phillips et al. |
| 7,309,325 B2 | 12/2007 | Mulier et al. |
| 7,323,004 B2 | 1/2008 | Parihar |
| 7,335,221 B2 | 2/2008 | Collier et al. |
| 7,347,812 B2 | 3/2008 | Mellier |
| 7,351,197 B2 | 4/2008 | Montpetit et al. |
| 7,357,773 B2 | 4/2008 | Watschke |
| 7,371,224 B2 | 5/2008 | Haischmann et al. |
| 7,377,936 B2 | 5/2008 | Gainor et al. |
| 7,479,115 B2 | 1/2009 | Savic |
| 7,500,945 B2 | 3/2009 | Cox et al. |
| 7,582,103 B2 | 9/2009 | Young et al. |
| 7,588,583 B2 | 9/2009 | Hamilton et al. |
| 7,637,918 B2 | 12/2009 | Dant |
| 7,686,821 B2 | 3/2010 | Hathaway et al. |
| 7,699,805 B2 | 4/2010 | Mulier et al. |
| 7,699,857 B2 | 4/2010 | Kim |
| 7,699,892 B2 | 4/2010 | Rafiee et al. |
| 7,776,059 B2 | 8/2010 | Craig |
| 7,780,700 B2 | 8/2010 | Frazier et al. |
| 7,794,471 B1 | 9/2010 | Bender et al. |
| 2003/0074023 A1 | 4/2003 | Kaplan et al. |
| 2003/0225420 A1 | 12/2003 | Wardle |
| 2006/0036265 A1 | 2/2006 | Dant |
| 2009/0142275 A1 | 6/2009 | Phillips et al. |
| 2011/0029000 A1 | 2/2011 | Lavi et al. |

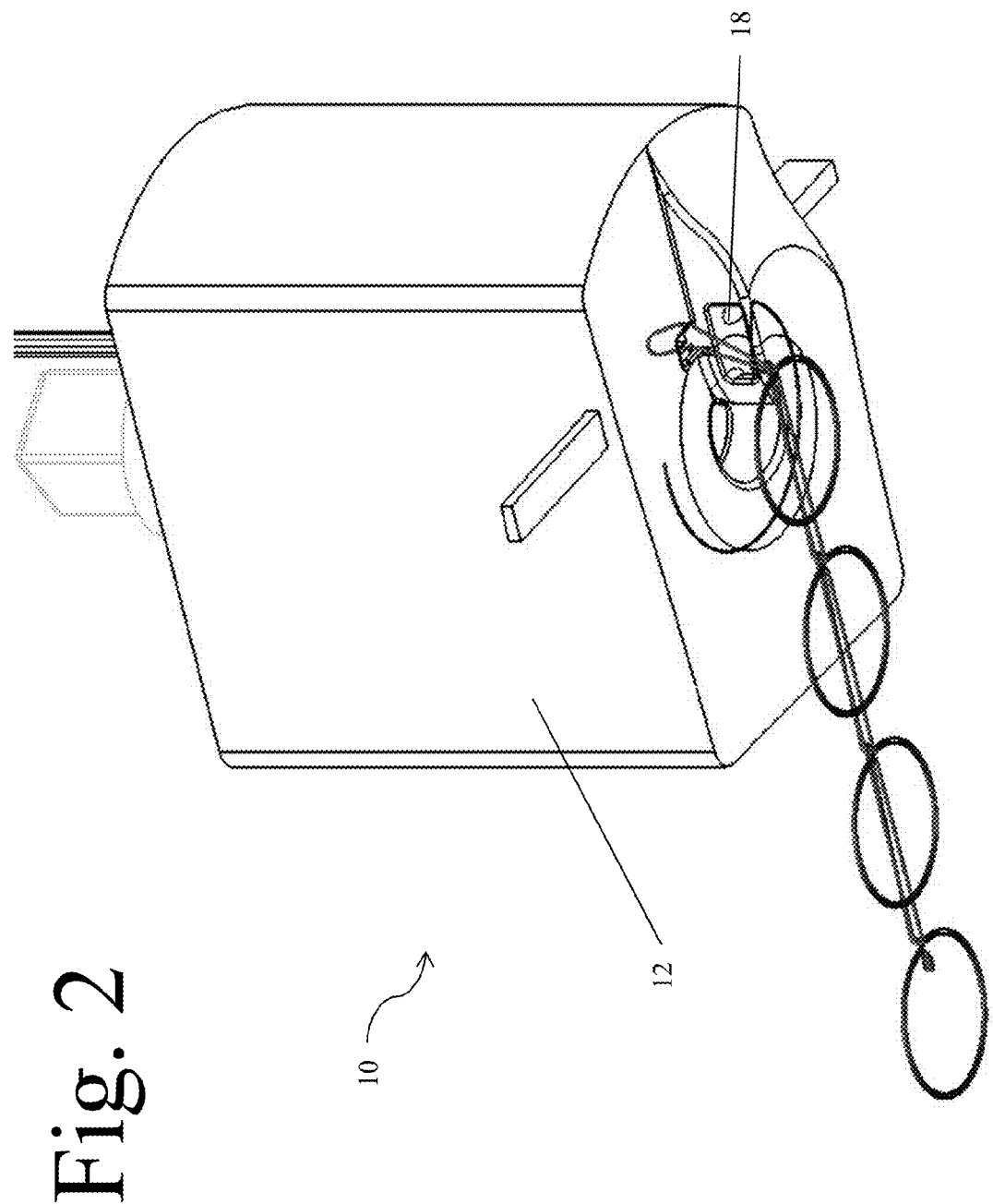

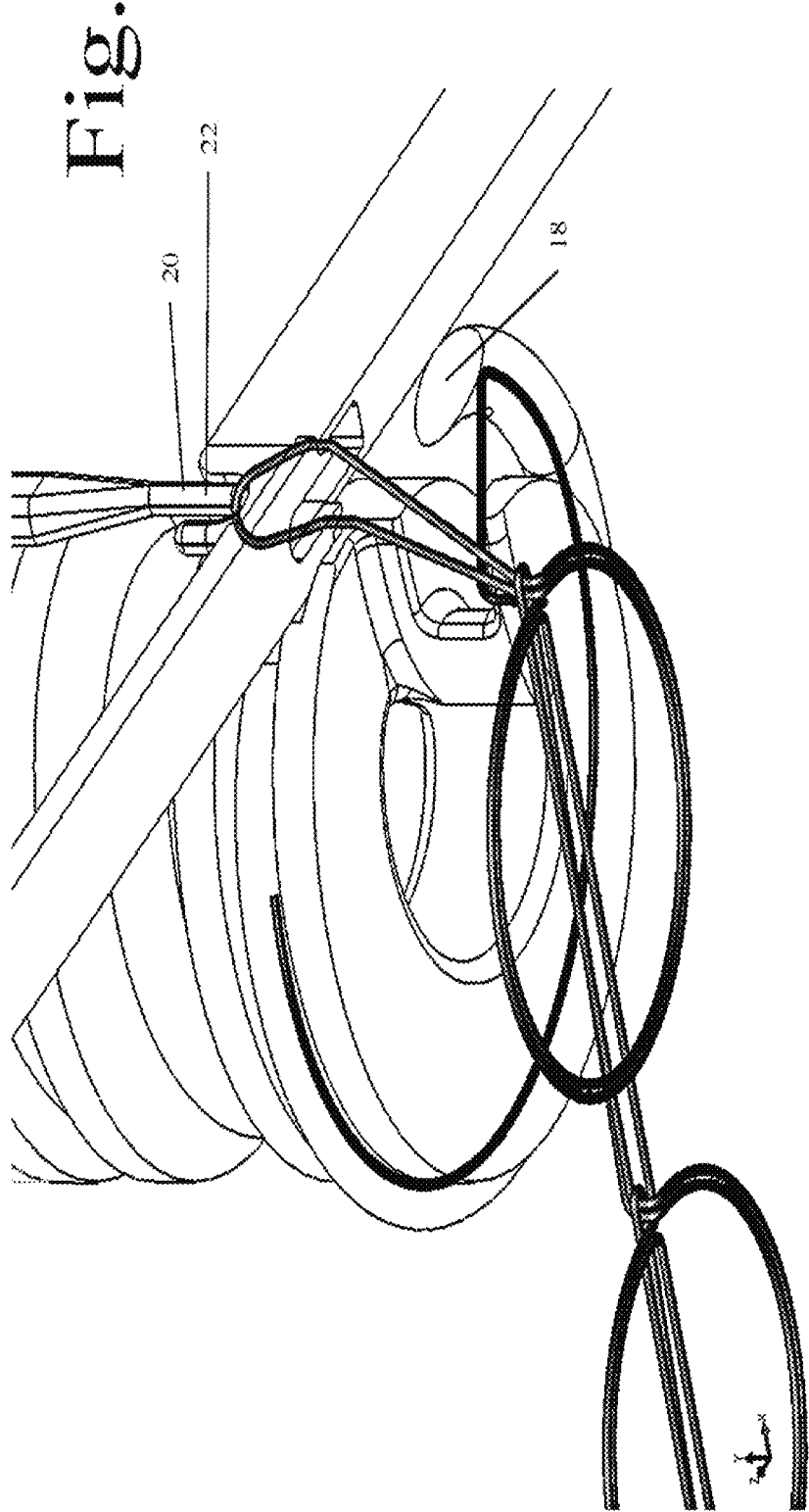

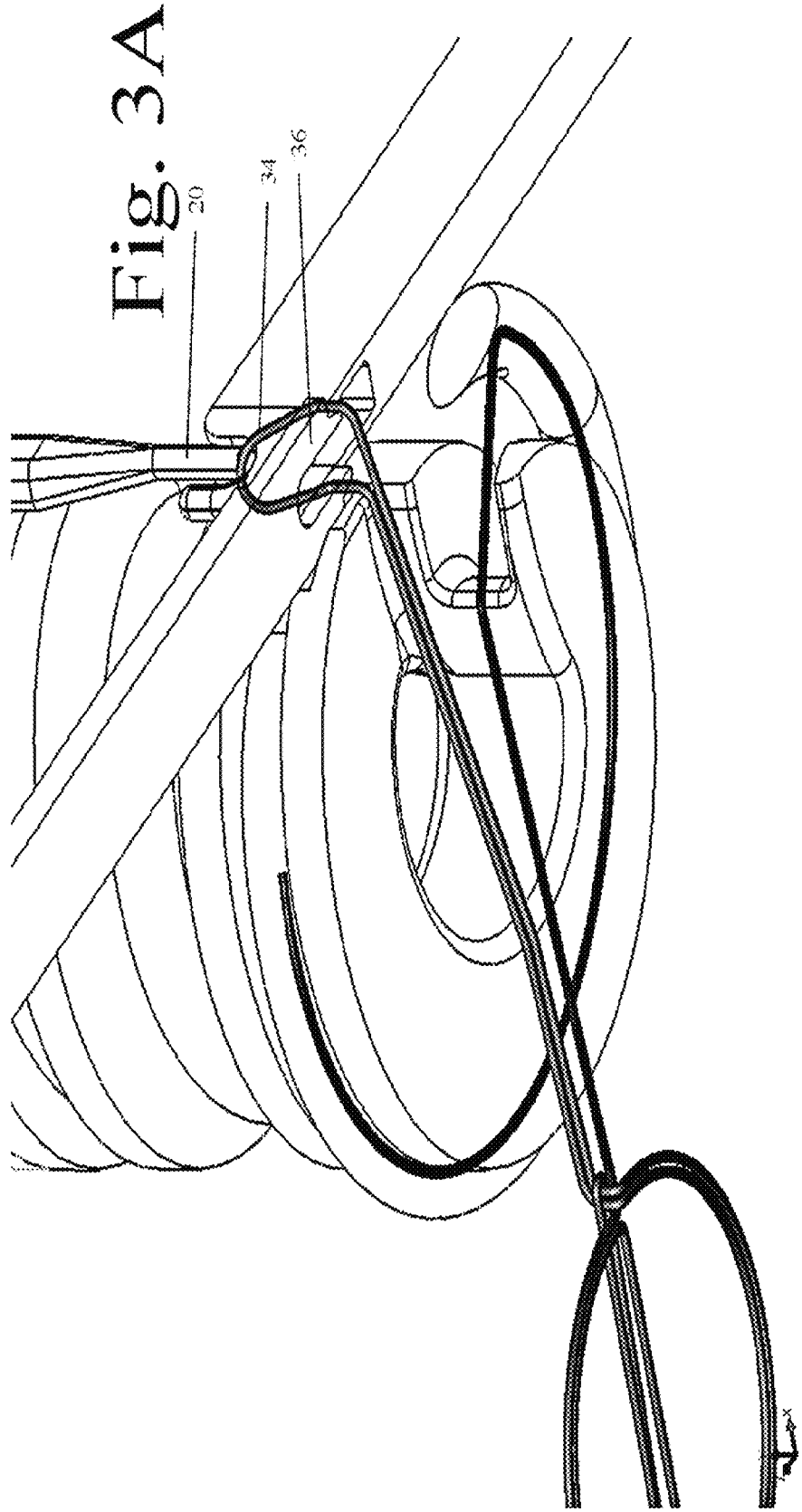

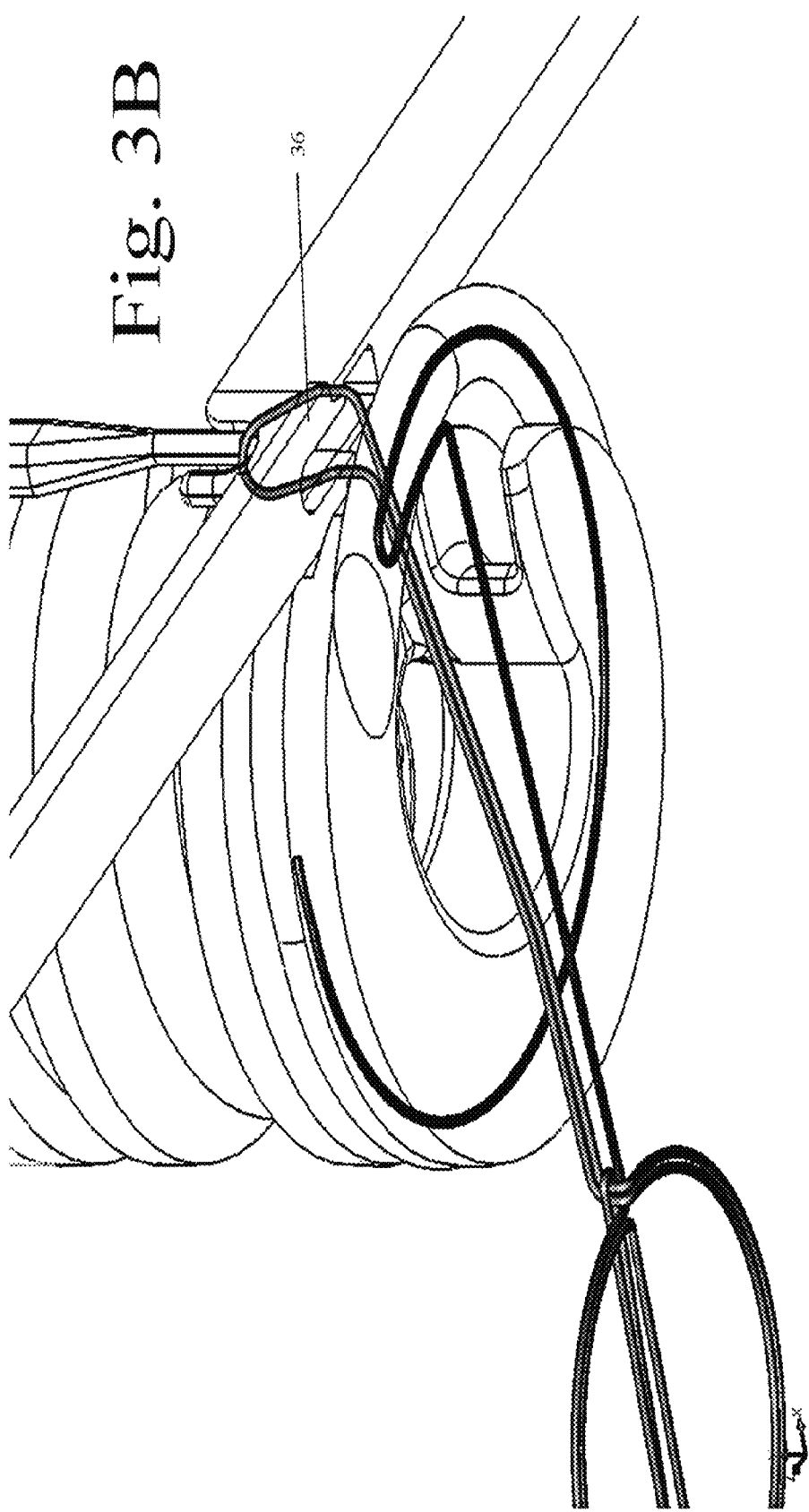

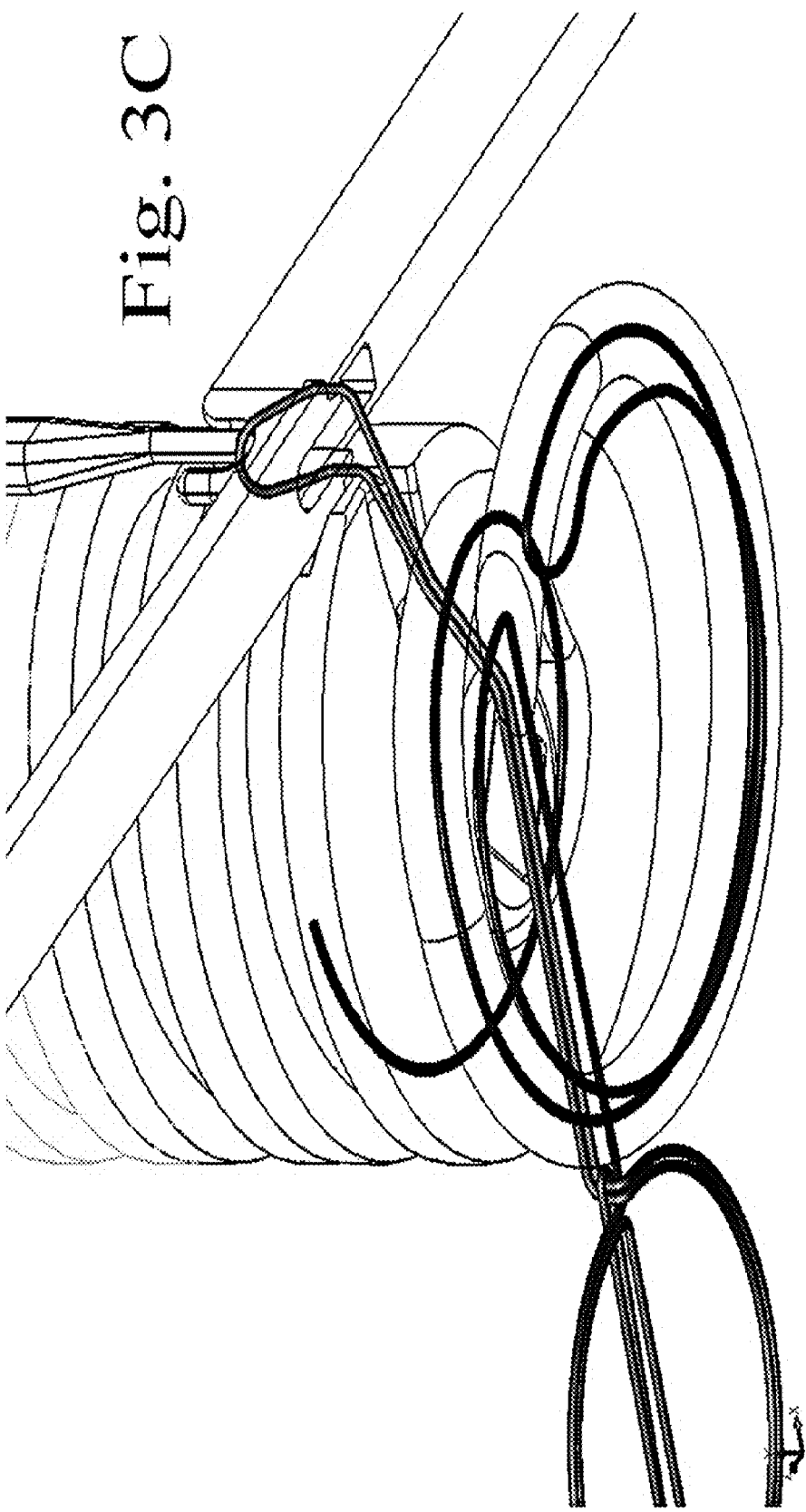

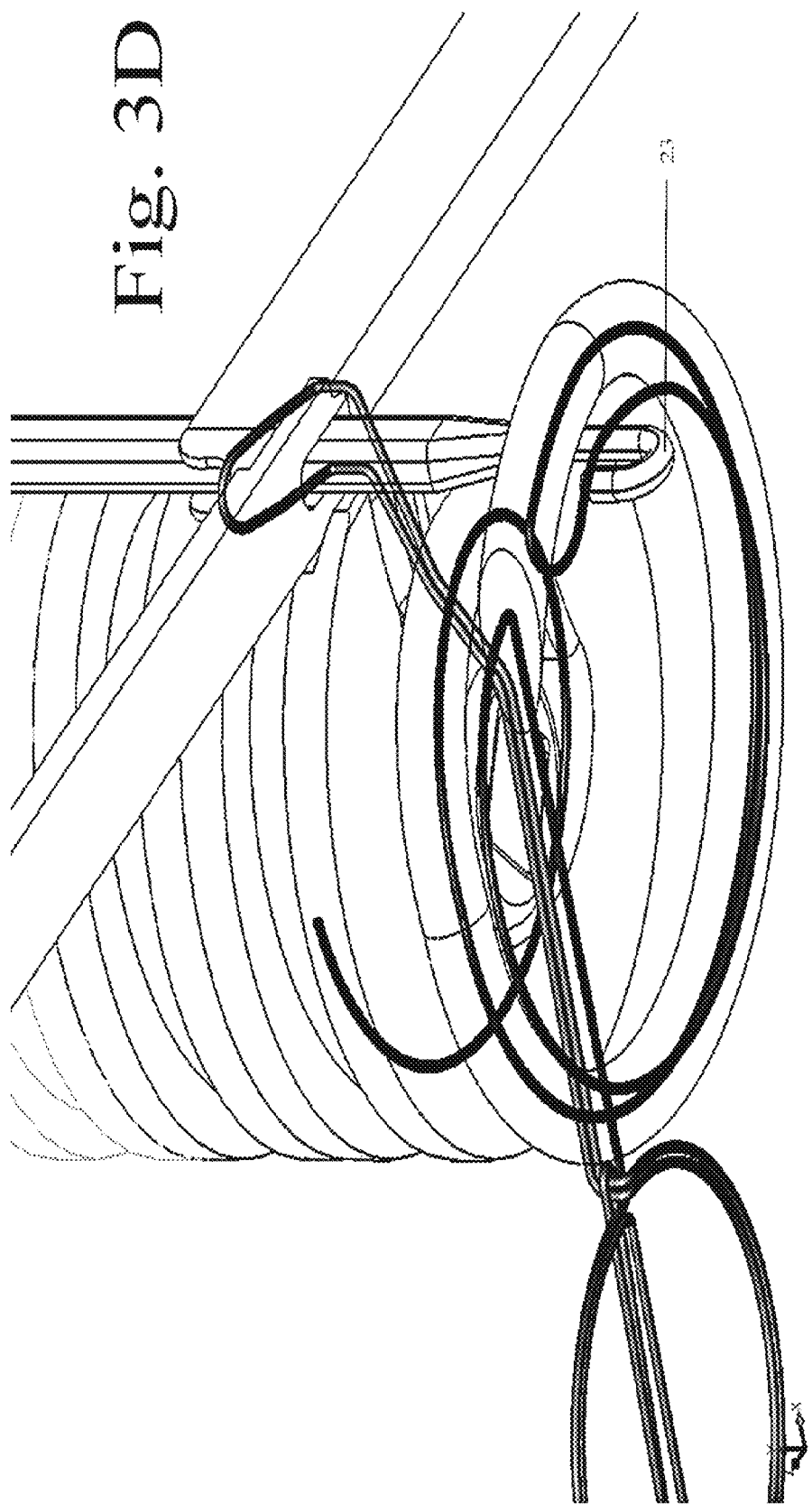

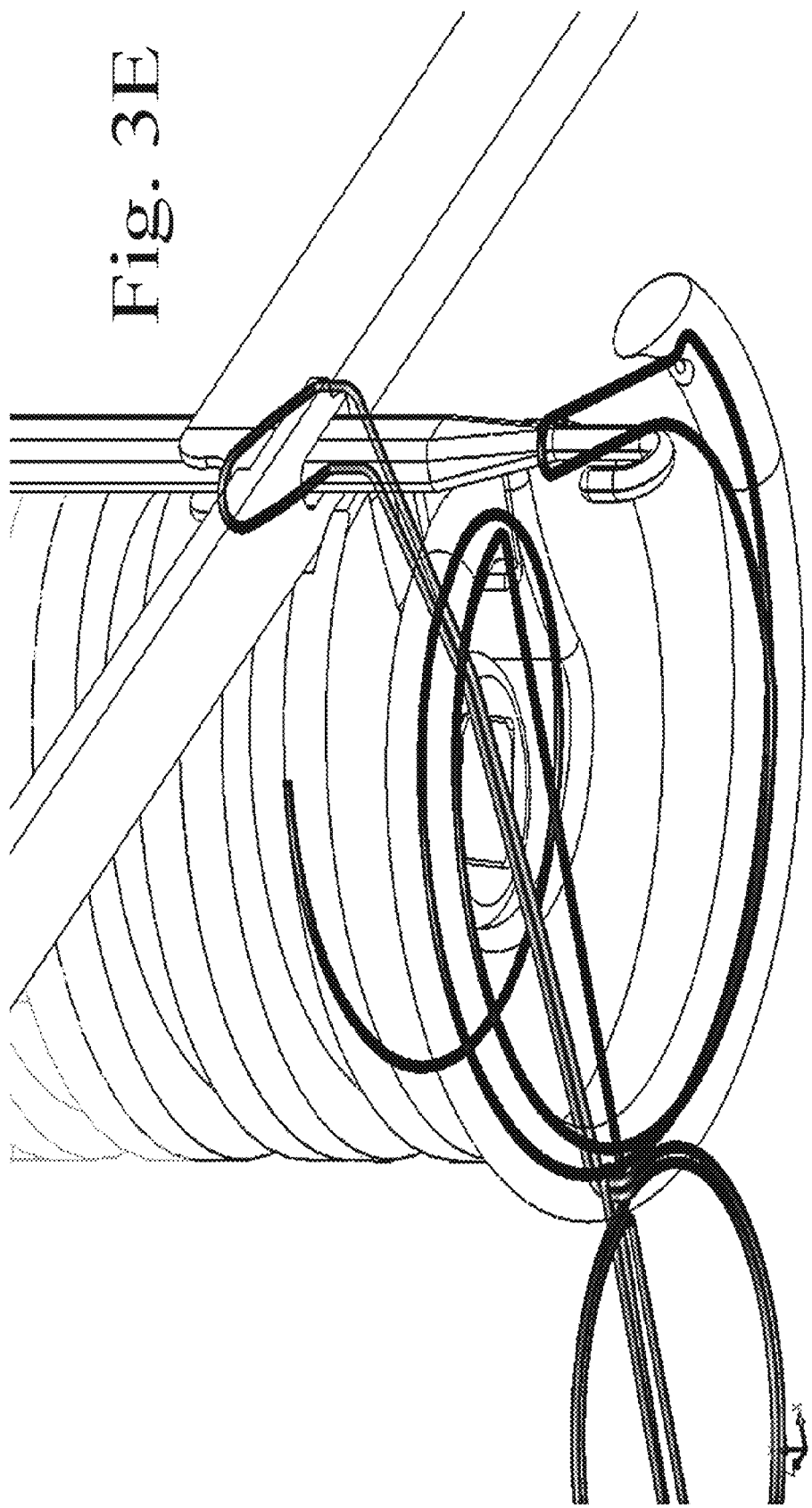

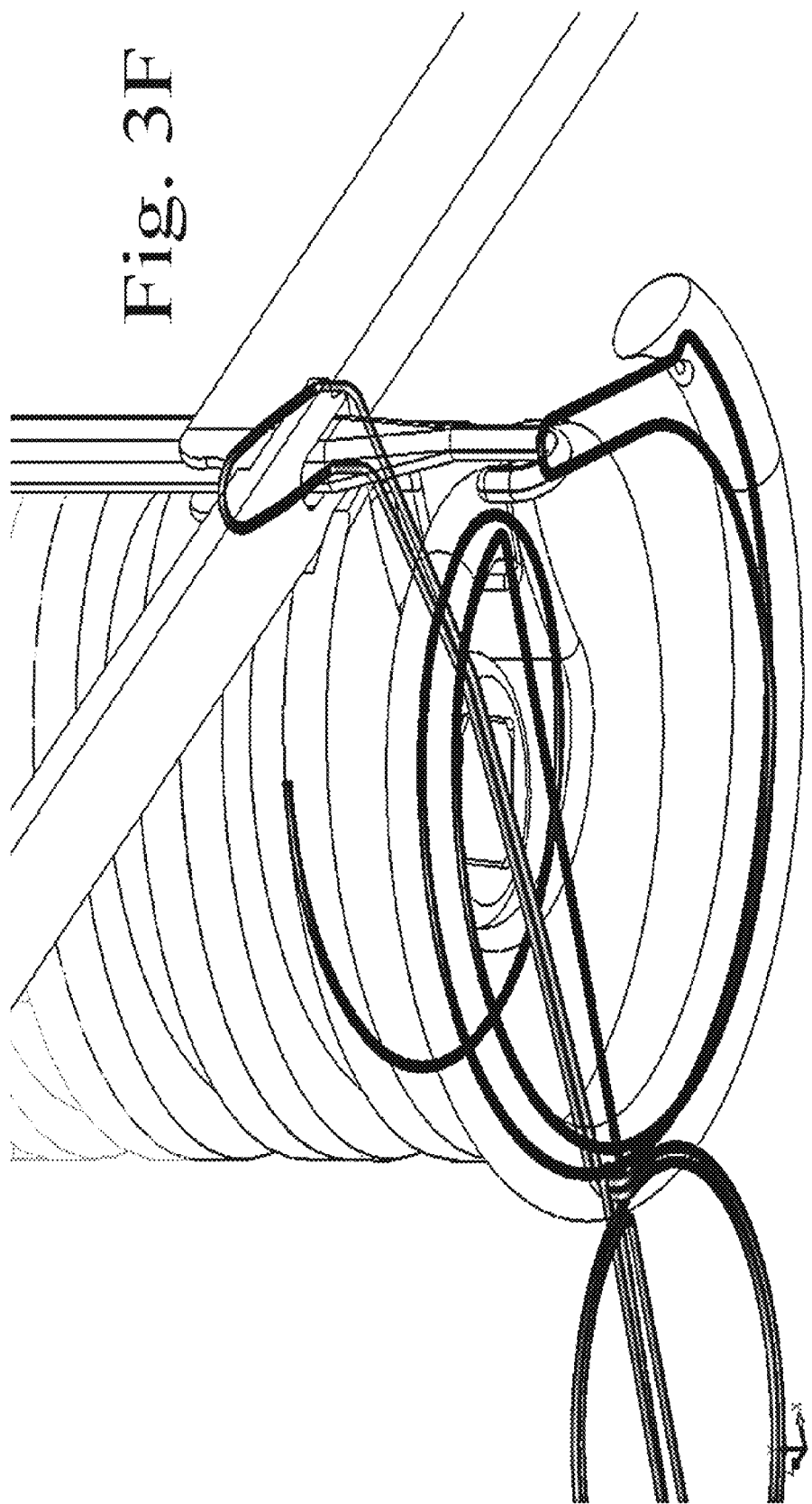

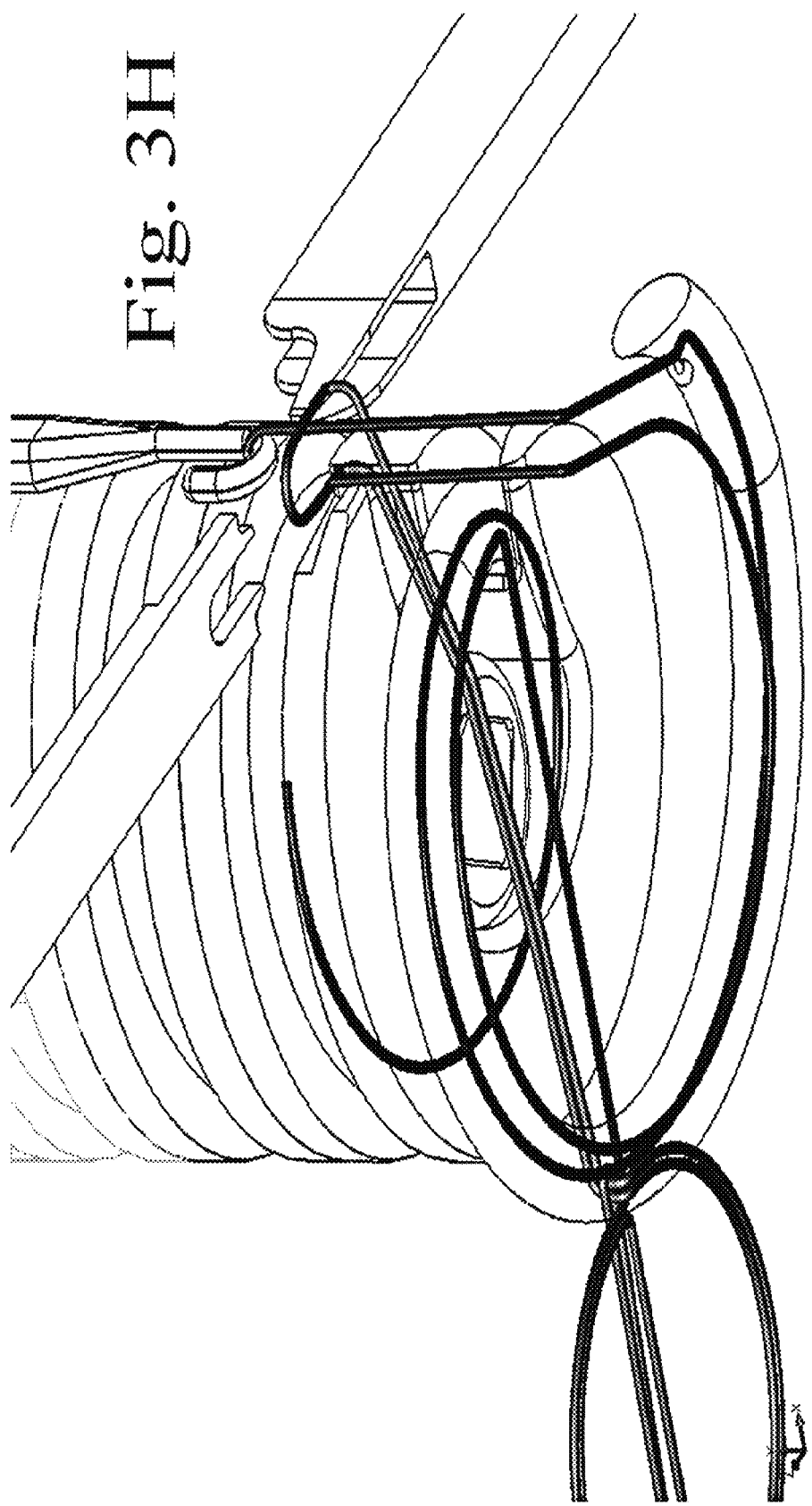

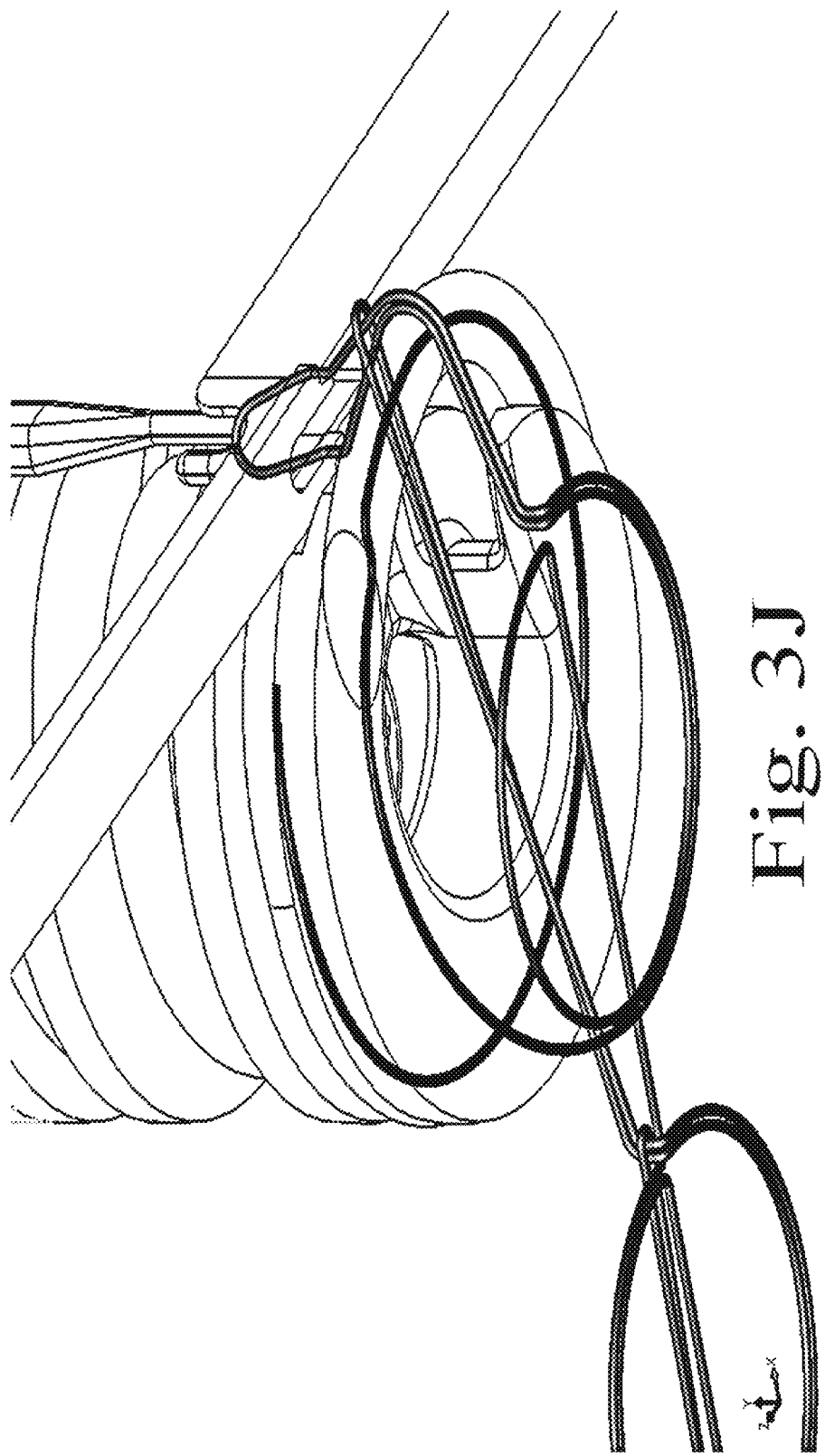

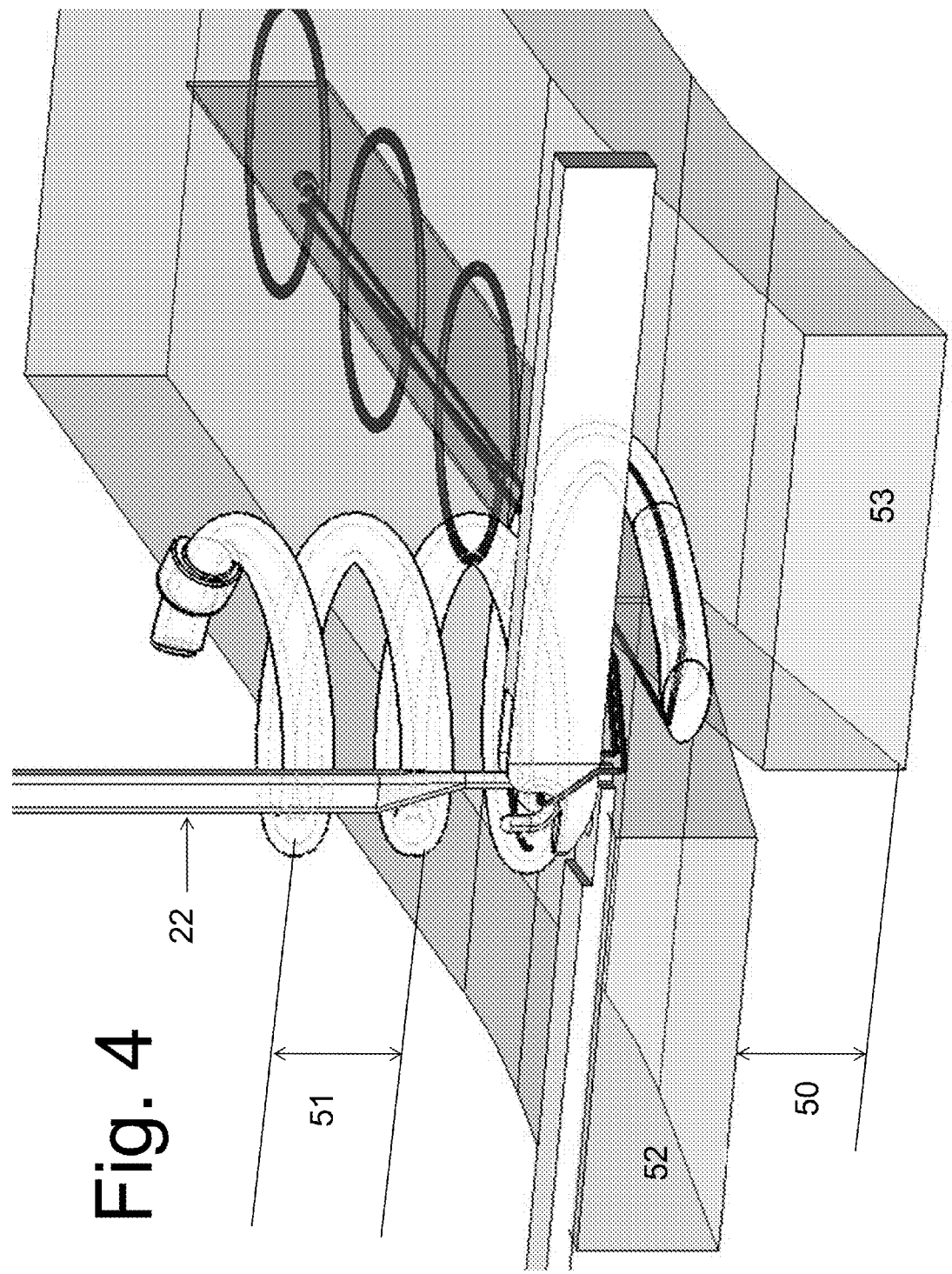

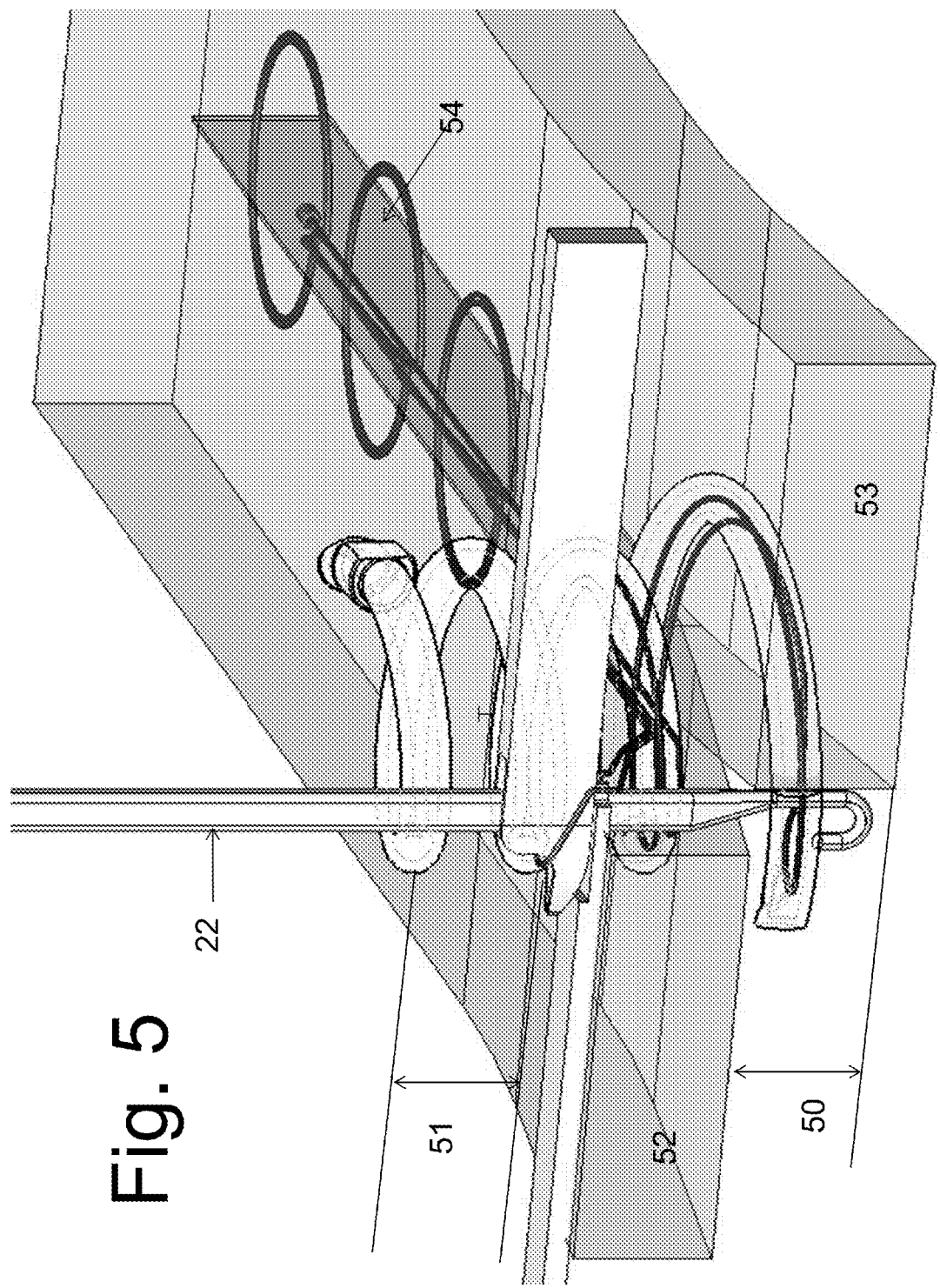

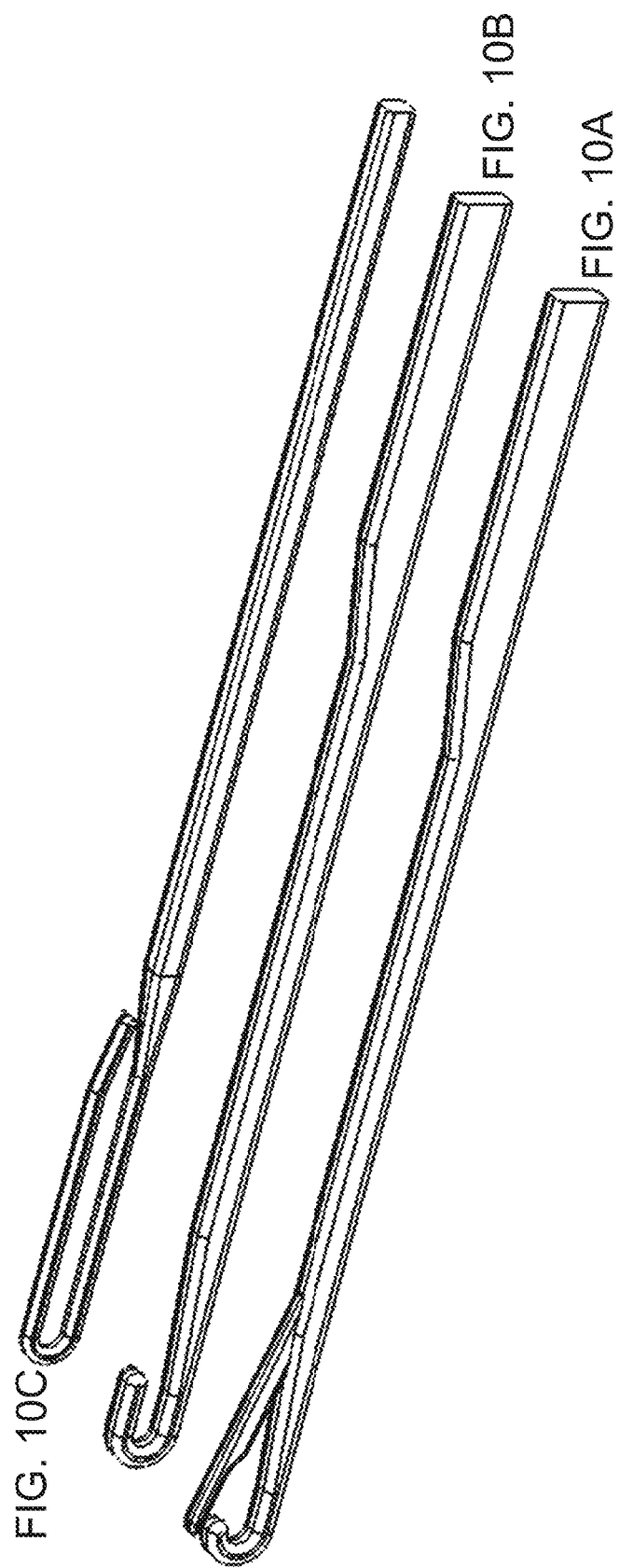

| Row | Ethicon* Sutures | Material | Natural/Synthetic | Construction |
|---|---|---|---|---|
| 1 | FAST ABSORBING SURGICAL GUT | Beef Serosa or Sheep Submucosa | Natural | Monofilament (Virtual) |
| 2 | SURGICAL GUT Plain | Beef Serosa or Sheep Submucosa | Natural | Monofilament (Virtual) |
| 3 | SURGICAL GUT Chromic | Beef Serosa or Sheep Submucosa | Natural | Monofilament (Virtual) |
| 4 | Coated VICRYL *RAPIDE* * (polyglactin 910) Suture | Polyglactin 910 | Synthetic | Braided |
| 5 | Coated VICRYL* (polyglactin 910) | Polyglactin 910 | Synthetic | Braided |
| 6 | Coated VICRYL* (polyglactin 910) Monofilament | Polyglactin 910 | Synthetic | Monofilament |
| 7 | Coated VICRYL* PLUS (polyglactin 910) | Polyglactin 910 | Synthetic | Braided |
| 8 | MONOCRYL* (poliglecaprone 25) Undyed | Poliglecaprone 25 | Synthetic | Monofilament |
| 9 | MONOCRYL* (poliglecaprone 25) Dyed | Poliglecaprone 25 | Synthetic | Monofilament |
| 10 | PDS* II (polydioxanone) | Polydioxanone | Synthetic | Monofilament |
| 11 | PERMA-HAND* SILK | Silk | Natural | Braided |
| 12 | SURGICAL STAINLESS STEEL | 316L Stainless Steel | Natural Alloy | Monofilament |
| 13 | NUROLON* Braided Nylon | Nylon 6 | Synthetic | Braided |
| 14 | ETHILON* Nylon | Nylon 6 | Synthetic | Monofilament |
| 15 | MERSILENE* Polyester Fiber | Polyester / Dacron | Synthetic | Braided |
| 16 | MERSILENE* Polyester Fiber | Polyester / Dacron | Synthetic | Monofilament |
| 17 | ETHIBOND* *EXCEL* Polyester | Polyester / Dacron | Synthetic | Braided |
| 18 | PROLENE* Polypropylene | Polypropylene | Synthetic | Monofilament |
| 19 | PRONOVA* poly(hexafluoroproylene-VDF) | Polymer blend of poly (vinylidene fluoride) and poly (vinylidene fluoride-co-hexafluoropolypropylene) | Synthetic | Monofilament |

* Trademark          ** Trademark of Ciba Specialy Chemicals Corp.

FIG. 11A

| Row | Coating (if applicable) | Material Color | Available Size Range | Strength Retention | Absorption Time | Absorption Process |
|---|---|---|---|---|---|---|
| 1 | n/a | Yellowish-tan | 5/0 - 6/0 | 5-7 days[1] | 21-42 days | Proteolytic enzymatic digestion |
| 2 | n/a | Yellowish-tan | 3 - 7/0 | 7-10 days[1] | 70 days | Proteolytic enzymatic digestion |
| 3 | Chromic Salts | Brown Blue | 3 - 7/0 | 21-28 days[1] | 90 days | Proteolytic enzymatic digestion |
| 4 | Polyglactin 370 Calcium Sterate | Undyed (Natural) | 1 - 5/0 | 50% @ 5 days  0% @ 10-14 days | 42 days | Hydrolysis |
| 5 | Polyglactin 370 Calcium Sterate | Violet Undyed (Natural) | 3 - 8/0 | 75% @ 14 days 50% @ 21 days 25% @ 28 days[2] | 56-70 days (63 day avg.) | Hydrolysis |
| 6 | n/a | Violet Undyed (Natural) | 9/0 - 10/0 | 75% @ 14 days 40% @ 21 days | 56-70 days (63 day avg.) | Hydrolysis |
| 7 | Polyglactin 370 IRGACARE MP** (triclosan) | Violet Undyed (Natural) | 2 - 5/0 | 75% @ 14 days 50% @ 21 days 25% @ 28 days | 56-70 days (63 day avg.) | Hydrolysis |
| 8 | n/a | Undyed (Natural) | 2 - 6/0 | 50-60% @ 7 days 20-30% @ 14 days | 91-119 days | Hydrolysis |
| 9 | n/a | Violet | 2 - 6/0 | 60-70% @ 7 days 30-40% @ 14 days | 91-119 days | Hydrolysis |
| 10 | n/a | Violet Clear | 2 - 9/0 | 70 @ 2 weeks 50% @ 4 weeks 25% @ 6 weeks | 180-210 days | Slow Hydrolysis |
| 11 | Bees Wax | Black White | 5 - 9/0 | ~ 1 year | n/a | n/a |
| 12 | n/a | Metallic Silver | 7 - 10/0 | Indefinite | n/a | n/a |
| 13 | n/a | Black | 1 - 6/0 | 20% loss/year | n/a | n/a |
| 14 | n/a | Blk/Grn/Clr | 2 - 11/0 | 20% loss/year | n/a | n/a |
| 15 | n/a | Green White | 5 - 6/0 | Indefinite | | |
| 16 | n/a | Green | 10/0 - 11/0 | Indefinite | n/a | n/a |
| 17 | Polybutilate | Green White | 5 - 7/0 | Indefinite | n/a | n/a |
| 18 | n/a | Blue Clear | 2 - 10/0 | Indefinite | n/a | n/a |
| 19 | n/a | Blue Clear | 2 - 10/0 | Indefinite | n/a | n/a |

1 Estimated strength retention    2 Sizes 6/0 and larger

FIG. 11B

Suture Needle Information

3/8 Inch Circle

1/2 Inch Circle

Straight

FIG. 12C ─────────

3/8 Precision Point

1/2 Taper Point

3/8 Micropoint

SUTURE STITCHES FOR CONTINUOUS SURGICAL SUTURING

CROSS REFERENCE TO RELATED APPLICATIONS

This application is a continuation of and claims priority from U.S. patent application Ser. No. 14/966,690, filed Dec. 11, 2015, now U.S. Pat. No. 9,770,239, which is a continuation of and claims priority from U.S. patent application Ser. No. 13/898,103, filed May 20, 2013, now U.S. Pat. No. 9,220,498, which is a divisional of and claims priority from U.S. patent application Ser. No. 13/012,965, filed Jan. 25, 2011, now U.S. Pat. No. 8,465,504.

BACKGROUND OF THE INVENTION

1. Field of the Invention

The present invention relates to surgical suturing methods and devices, and particularly to devices, machines, methods, needles, and stitch designs for cosmetic-grade suturing for reduced or minimized scarring and/or for organ or tissue internal suturing.

2. Description of the Prior Art

It is generally known in the prior art to provide specialized needles and devices for suturing and for use with suture materials. Prior art patent documents include the following: U.S. Pat. No. 67,545 issued Aug. 6, 1867 for a spiral fissure needle; U.S. Pat. No. 196,226 issued Oct. 16, 1877 for a corkscrew; U.S. Pat. No. 242,602 issued Jun. 7, 1881 for a corkscrew; U.S. Pat. No. 349,791 issued Sep. 28, 1886 for a suture instrument; U.S. Pat. No. 919,138 issued Apr. 20, 1909 for a surgical needle; U.S. Pat. No. 1,583,271 issued May 4, 1926 for a surgical instrument; U.S. Pat. No. 2,327,353 issued Aug. 24, 1943 for an instrument for suturing; U.S. Pat. No. 2,959,172 issued Nov. 8, 1960 for a self-threading suture instrument; U.S. Pat. No. 3,037,619 issued Jun. 5, 1962 for suture devices.

Also, it is known in the prior art to include a tubular needle configuration, such as in U.S. Pat. No. 4,204,541 issued May 27, 1980 for a surgical instrument for stitching up soft tissues with lengths of spiked suture material describes a surgical instrument for stitching up soft tissues with lengths of spiked suture material that include a hollow body which houses a tubular needle having a through bore adapted to accommodate said length of suture material to be introduced into the tissue being sutured along with the needle, and a stop stationary with respect to the body and accommodated inside the through bore of the needle. Both the needle and the stop are shaped as coils having the same diameter and lead, and the needle is mounted slidably along the stop so as to retain the length of suture material in the tissue being sutured while extracting the needle therefrom.

It is also provided in the prior art to provide suturing instruments, such as the following:

U.S. Pat. No. 4,440,171 issued Apr. 3, 1984 for a suturing instrument and a method of holding a shuttle describes a surgical suturing instrument that crosses and knots a suturing thread combining a shuttle and the other suturing thread passing through an eye of a curved needle in a lock stitching practice, for accomplishing smooth passage of passing the shuttle through a loop of the needle thread and exact combination of the shuttle thread and the needle thread without getting out the shuttle from a shuttle holder during the suturing operation so as to form sound suturing stitchings every time. The shuttle is accommodated between a shuttle holder and a shuttle claw. The shuttle is formed with a front end portion movable between a guide groove in the shuttle claw and a guide groove in the shuttle holder. The shuttle is further formed with a sharp end for catching a thread loop in the suturing operation.

U.S. Pat. No. 4,465,070 issued Aug. 14, 1984 for a stitching formation by a suturing instrument describes a suturing instrument used to form stitchings including stitching formation made by causing a shuttle thread to move in reciprocation on cut edges of a human part, between knottings and next knottings in a lock stitching, via an outer side of a needle thread at a needle-out-hole from a needle-in-hole of a needle, thereby to make conglutination of the cut part stable and sound.

U.S. Pat. No. 4,524,771 issued Jun. 25, 1985 for a multiple curved surgical needle describes a needle which includes a plurality of curves which provide for improved control while suturing.

U.S. Pat. No. 4,641,652 issued Feb. 10, 1987 for a applicator for tying sewing threads describes an applicator for utilization in combination with an endoscope tube includes a coil connected to a longitudinal passage through a shaft and comprising hollow turns connected to the shaft passage for reception of a sewing thread, whose proximal extremity is passed through a loop projecting from a radial opening at the distal extremity of the shaft, is then drawn through the shaft passage and fastened to the proximal shaft extremity. Tying the single stitch after piercing the tissues is performed by passing the needle axially through the coil and then around the thread and twisting the coil out of the loop formed thereby to form the first half of a knot which is then complemented by the second half of the knot tied in the same way, the knot being tied by subsequently pulling together the two said halves.

U.S. Pat. No. 4,969,892 issued Nov. 13, 1990 for a suturing anchoring device for use in a female suspension procedure describes an anchoring means for anchoring a suture in tissue includes a housing, a substantially cylindrical means within said housing for receiving a suture, and an adjusting means. Another anchoring means includes a housing, a rotating spool within said housing, a driving gear, and an adjusting means.

U.S. Pat. No. 5,152,769 issued Oct. 6, 1992 for an apparatus for laparoscopic suturing with improved suture needle describes a novel suturing assembly defined by a new and improved suturing needle, having a bore therethrough for forming an arc of thread to be grasped. The assembly would comprise a first and second barrel portion, the portions working to allow a rod member to secure the arc of thread formed, and hold it in place, while the needle forms a second suture, and secures the loop as part of the suture.

U.S. Pat. No. 5,356,424 issued Oct. 18, 1994 for a laparoscopic suturing device describes a laparoscopic suturing device that includes a suturing needle and a driver for manipulating the needle.

U.S. Pat. No. 5,499,991 issued Mar. 19, 1996 for an endoscopic needle with suture retriever describes a suture retriever and method for manipulating suture during endoscopic surgical procedures.

U.S. Pat. No. 5,507,743 issued Apr. 16, 1996 for a coiled RF electrode treatment apparatus describes an RF treatment apparatus provides multi-modality treatment for tumors and other desired tissue masses, and includes an RF indifferent electrode and an active electrode.

U.S. Pat. No. 5,520,703 issued May 28, 1996 for a laparoscopic deschamp and associated suturing technique describes a laparoscopic suturing device with an elongate shaft having a distal end and a proximal end and an arcuate tissue piercing element permanently fixed to the shaft at the distal end, the arcuate tissue piercing element lying in a plane disposed substantially transversely to the shaft. The tissue piercing element is provided at a free end, spaced from the shaft, with an eyelet, and the device has a suture thread extending through the eyelet.

U.S. Pat. No. 5,562,685 issued Oct. 8, 1996 for a surgical instrument for placing suture or fasteners and U.S. Pat. No. 5,709,692 issued Jan. 20, 1998 for a surgical instrument for placing suture or fasteners at a remote location such as a laparoscopic surgery. The instrument is an elongated handle having a coiled projection at its distal end. The coiled projection is employed in penetrating and positioning a length of suture or fastener in tissue, for example, as in tissue proximation.

U.S. Pat. No. 5,810,851 issued Sep. 22, 1998 for a suture spring device describes a guide used to position a suture spring device in anatomical tissue in an elastically deformed, expanded state and is subsequently removed to permit the suture spring device to move from the elastically deformed, expanded state toward a relaxed, contracted state to apply a predetermined compression to the tissue engaged by the device.

U.S. Pat. No. 5,911,689 issued Jun. 15, 1999 for a subcutaneous radiation reflection probe describes a subcutaneous radiation reflection probe for measuring oxygen saturation in living tissue includes an elongate drive shaft on one end of which is detachably coupled a mounting cup.

U.S. Pat. No. 5,935,138 issued Aug. 10, 1999 for a spiral needle for endoscopic surgery describes a needle for endoscopic surgery is curved into an arc of more than 180.degree. And twisted, so that it forms a part of a spiral, with a lateral offset between the needle point and barrel.

U.S. Pat. No. 5,947,983 issued Sep. 7, 1999 for a tissue cutting and stitching device and method describes a device for cutting tissue, the device comprising a first tube having a side window; a second tube positioned within the first tube, the second tube having a side window and being movable within the first tube; a third tube positioned within the second tube, the third tube having a side window and being movable within the second tube; and a needle insertable within the second tube, the needle housing a suture.

U.S. Pat. No. 6,113,610 issued Sep. 5, 2000 for a device and method for suturing wound describes a needle assembly in which the needle is constructed of a spring-like material and initially housed within a sheath in a deformed condition. The needle can be easily exposed by sliding an actuator so as to release the constraining means and allow the needle to assume its undeformed condition.

U.S. Pat. No. 6,520,973 issued Feb. 18, 2003 for an anastomosis device having an improved needle driver describes an anastomosis device for attaching a first hollow vessel to a second hollow vessel. The device includes a handle for holding the device, and a head assembly, attached to the handle, for holding the first and second hollow vessels adjacent to each other. The head assembly having a distal end, a proximal end and a longitudinal axis there between. The device further includes a needle guide disposed longitudinally along the head assembly adjacent to the vessels, and a helical needle, having a suture attached to a proximal end thereof, disposed within the head assembly at its proximal end. The device has an actuator on the handle for actuating a needle driver. The needle driver is coupled to the head and includes a flexible rotatable member operated by the actuator, for rotating and driving the needle distally along the needle guides and through the first and second hollow vessels.

U.S. Pat. No. 6,537,248 issued Mar. 25, 2003 for a helical needle apparatus for creating a virtual electrode used for the ablation of tissue describes a surgical apparatus for delivering a conductive fluid to a target site for subsequent formation of a virtual electrode to ablate bodily tissue at the target site by applying a current to the delivered conductive fluid. The surgical apparatus includes an elongated device forming a helical needle.

U.S. Pat. No. 6,562,052 issued May 13, 2003 for a suturing device and method that allows a physician to remotely suture biological tissue.

U.S. Pat. No. 6,613,058 issued Sep. 2, 2003 for an anastomosis device having needle receiver for capturing the needle after it has passed through the needle guide.

U.S. Pat. No. 6,626,917 issued Sep. 30, 2003 for a helical suture instrument which either pushes or pulls a suture along a helical needle tract.

U.S. Pat. No. 6,663,633 issued Dec. 16, 2003 for a helical orthopedic fixation and reduction device, insertion system, and associated methods describes a system for fixation of a soft tissue tear includes a flexible, generally helical fixation element biased to a predetermined pitch and a hollow, generally helical insertion element dimensioned to admit at least a distal portion of the fixation element into a lumen thereof.

U.S. Pat. No. 6,723,107 issued Apr. 20, 2004 for a method and apparatus for suturing describes devices and techniques for suturing that are particularly useful in laparoscopic, arthroscopic, and/or open surgical procedures. A method of delivering a suture includes providing a suture device, releasably coupling a suture to a distal end of a suture device by threading the suture through a first region of a bounded opening of the suture device and moving the suture to a second region of the bounded opening having a dimension smaller than a diameter of the suture to trap the suture in the second region, penetrating a substrate with the distal end of the suture device such that the a portion of the suture passes through the substrate, and releasing the suture from the distal end of the suture device.

U.S. Pat. No. 6,911,003 issued Jun. 28, 2005 for transobturator surgical articles and methods describes surgical articles, implants and components suitable for a transobturator surgical procedure.

U.S. Pat. No. 6,911,019 issued Jun. 28, 2005 for a helical needle apparatus for creating a virtual electrode used for the ablation of tissue describes a surgical apparatus for delivering a conductive fluid to a target site for subsequent formation of a virtual electrode to ablate bodily tissue at the target site by applying a current to the delivered conductive fluid.

U.S. Pat. No. 6,911,037 issued Jun. 28, 2005 for a retrievable septal defect closure device describes a septal defect closure device having a first occluding disk having a first flexible membrane attached to a first frame and a second occluding disk having a second flexible membrane attached to a separate second frame. The first frame has at least two outwardly extending loops joined to one another by flexible joints. These loops are attached to the first membrane to define taut fabric petals when the first disk is in a deployed configuration.

U.S. Pat. No. 6,923,807 issued Aug. 2, 2005 for a helical device and method for aiding the ablation and assessment of tissue describes a helical needle attached to a surgical probe to aid in the insertion of the probe into a tissue mass.

U.S. Pat. No. 6,986,776 issued Jan. 17, 2006 for a suturing apparatus, method and system describes an apparatus used with a helical suture device has a first end and a second end. The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

U.S. Pat. No. 7,070,556 issued Jul. 4, 2006 for transobturator surgical articles and methods describes a surgical instrument and method for treating female urinary stress incontinence. The instrument includes a first curved needle-like element defining in part a curved shaft having a distal end and a proximal, a mesh for implanting into the lower abdomen of a female to provide support to the urethra; a second curved needle element having a proximal end and a distal end, and a coupler for simultaneous attachment to the distal end of the first needle and the distal end of the second needle.

U.S. Pat. No. D543,626 issued May 29, 2007 for a handle for a surgical instrument describes an ornamental design for a handle for a surgical instrument U.S. Pat. No. 7,235,087 issued Jun. 26, 2007 for an articulating suturing device and method describes devices, systems, and methods for suturing of body lumens allow the suturing of vascular puncture sites located at the distal end of a percutaneous tissue tract.

U.S. Pat. No. 7,269,324 issued Sep. 11, 2007 for a helical fiber optic mode scrambler describes methods and apparatus of the present invention provide advantages for remote laser delivery systems that conduct high levels of light energy through a fiber optic cable to a selectable target surface.

U.S. Pat. No. 7,288,105 issued Oct. 30, 2007 for a tissue opening occluder describes a tissue opening occluder including first and second occluder portions, each occluder portion including a frame structure and an attachment structure to attach one portion to the other portion. The frames may be utilized to constrain the tissue between the two portions enough to restrict the significant passage of blood therethrough.

U.S. Pat. No. 7,290,494 issued Nov. 6, 2007 for a method for manufacturing stent-grafts describes a sewing machine which is capable of sewing reinforcing wire to tubular grafts in order to form stent grafts. A bobbin (which may be seated in a shuttle) carries a bottom thread through the bore of the tubular graft and forms a stitch in combination with a top thread carried on a needle which pierces the graft wall.

U.S. Pat. No. 7,309,325 issued Dec. 18, 2007 for a helical needle apparatus for creating a virtual electrode used for the ablation of tissue describes a surgical apparatus for delivering a conductive fluid to a target site for subsequent formation of a virtual electrode to ablate bodily tissue at the target site by applying a current to the delivered conductive fluid.

U.S. Pat. No. 7,323,004 issued Jan. 29, 2008 for a device for providing automatic stitching of an incision describes an automatic suturing device including: a body for insertion into an opening in tissue; a plurality of hooks movably disposed in the body between retracted and extended positions; a suture holder having sutures disposed therein, the suture holder having a mechanism for engaging a portion of the hooks when in the retracted position and for attaching the sutures to a portion of the plurality of hooks; and an actuator for actuating the plurality of hooks from the retracted position to the extended position and for embedding the exposed plurality of hooks with the attached sutures into the tissue surrounding the opening.

U.S. Pat. No. 7,335,221 issued Feb. 26, 2008 for a suture anchoring and tensioning device and method for using same describes a suture anchoring device made from a coiled member having a helical configuration with a multiplicity of turns. When used in connection with a surgical procedure, the device is positioned adjacent to a wound site and a suture is attached to at least two of the turns so as to anchor the suture to the coiled member.

U.S. Pat. No. 7,347,812 issued Mar. 25, 2008 for prolapse repair instruments.

U.S. Pat. No. 7,351,197 issued Apr. 1, 2008 for a method and apparatus for cystocele repair describes comprising the steps of: establishing four pathways in tissue around a bladder of a patient, introducing a strap into each of said pathways, and positioning beneath said bladder of said patient a support member having each said strap connected thereto such that said bladder of said patient is supported by said support member and a bulge of said bladder into a vagina of said patient is reduced.

U.S. Pat. No. 7,357,773 issued Apr. 15, 2008 for a handle and surgical article describes handles for needles suitable for pelvic floor surgical procedures.

U.S. Pat. No. 7,371,244 issued May 13, 2008 for a deployment apparatus for suture anchoring device describes a deployment device for anchoring a suture to a suture anchoring device, which is made from a helically coiled member, includes a winding tube for winding a suture around the coiled member in a helical path such that the suture is attached to at least one turn of the coiled member.

U.S. Pat. No. 7,377,936 issued May 27, 2008 for a retrievable septal defect closure device describes a septal defect closure device having a first occluding disk having a first flexible membrane attached to a first frame and a second occluding disk having a second flexible membrane attached to a separate second frame. The first frame has at least two outwardly extending loops joined to one another by flexible joints. These loops are attached to the first membrane to define taut fabric petals when the first disk is in a deployed configuration.

U.S. Pat. No. 7,479,155 issued Jan. 20, 2009 for a defect occluder release assembly and method describes a release assembly is provided to aid the reversible and repositionable deployment of a defect occluder. The release assembly includes an occluder tether having a distal portion comprising at least one suture loop, and a snare structure having a distal portion comprising a snare element. The at least one suture loop is receivable through at least a portion of the defect occluder, and reversibly looped over an anchor element so as to permit reversible collapse the defect occluder for selective ingress and egress from a delivery catheter. The snare element is reversibly engageable with the anchor element so as to reversibly retain the at least one suture loop upon the anchor element, and thereby hold the defect occluder in a posture for reversible free-floating tethered deployment in a defect while being observable in a final position prior to release.

U.S. Pat. No. 7,500,945 issued Mar. 10, 2009 for a method and apparatus for treating pelvic organ prolapse describes the steps of establishing a first pathway between the external perirectal region of the patient to the region of the ischial spine in tissue on one side of the prolapsed organ, followed by establishing a second pathway in tissue on the contralateral side of the prolapsed organ. A support member, which includes a central support portion and two end portions, is positioned in a position to reposition said prolapsed organ in said organ's anatomically correct location. The end portions of the support member are introduced through the respective tissue pathways, followed by adjustment of the end portions so that the support member is located in a therapeutic relationship to the prolapsed organ that is to be supported.

U.S. Pat. No. 7,582,103 issued Sep. 1, 2009 for a tissue opening occluder describes a tissue opening occluder comprising first and second occluder portions, each occluder portion including a frame structure and an attachment structure to attach one portion to the other portion. The frames may be utilized to constrain the tissue between the two portions enough to restrict the significant passage of blood therethrough.

U.S. Pat. No. 7,588,583 issued Sep. 15, 2009 for a suturing device, system and method describes improved medical suturing devices, systems, and methods to hold a suture needle at a fixed location relative to a handle of the device, allowing the surgeon to grasp and manipulate the handle of the suturing device to insert the needle through tissues in a manner analogous to use of a standard needle gripper.

U.S. Pat. No. 7,637,918 issued Dec. 29, 2009 for a helical suturing device describes an apparatus for repairing a tear in an annulus fibrosus of a spinal disc includes a hollow, helically-shaped suturing needle and a retriever.

U.S. Pat. No. 7,686,821 issued Mar. 30, 2010 for a apparatus and method for positive closure of an internal tissue membrane opening describes a device having two components: a needle advancing apparatus slidable longitudinally along a catheter to advance needles into a tissue membrane, such as a blood vessel wall, around an opening in the membrane; and, a suture retrieval assembly insertable through the catheter beyond a distal side of the tissue membrane.

U.S. Pat. No. 7,699,805 issued Apr. 20, 2010 for a helical coil apparatus for ablation of tissue describes a surgical apparatus for delivering a conductive fluid to a target site for subsequent formation of a virtual electrode to ablate bodily tissue at the target site by applying a current to the delivered conductive fluid.

U.S. Pat. No. 7,699,857 issued Apr. 20, 2010 for a hydrodynamic suture passer describes a hydrodynamic suturing instrument, comprises a elongated cannulated suturing needle having a distal end configured to carry a suture through tissue and a proximal end adapted to connect to a syringe barrel and a lumen extending from said proximal end to an opening at the distal end for having a size for the passage of a suture, and the opening at the distal end configured to receive a suture extending from the lumen along an outer surface of the needle wherein a sharp point extends forward of the suture. A companion instrument includes forceps having a distal end with jaws and a proximal end with a lumen extending from the proximal end to the distal end for passage of the needle, and the jaws having an opening enabling passage of the needle through tissue grasped in the jaws.

U.S. Pat. No. 7,699,892 issued Apr. 20, 2010 for a minimally invasive procedure for implanting an annuloplasty device describes a method for modifying a heart valve annulus includes placing a purse string suture at a puncture site adjacent a heart valve, inserting at least one delivery member through the puncture site, positioning a distal end of the at least one delivery member adjacent a portion of a valve annulus, deploying an annuloplasty device carried within the at least one delivery member and implanting the annuloplasty device into the valve annulus. The method also includes reshaping the heart valve annulus after implantation of the at least one annuloplasty device.

U.S. Pat. No. 7,776,059 issued Aug. 17, 2010 for a suturing method describes an apparatus used with a helical suture device has a first end and a second end. The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

U.S. Pat. No. 7,780,700 issued Aug. 24, 2010 for a patent foramen ovale closure system describes a patent foramen ovale closure device, method of delivering and a delivery system are provided. The device may include a closure device releasably connectable to an actuator. The device may include a proximal segment, an intermediate segment and a distal segment. When delivered, the proximal segment and intermediate segment form a first clip-shaped portion sized and configured to be positioned over a septum secundum of the patent foramen ovale, and the intermediate segment and distal segment form a second clip-shaped portion sized and configured to be positioned over a septum primum of the patent foramen ovale.

U.S. Pat. No. 7,794,471 issued Sep. 14, 2010 for a compliant anastomosis system describes an integrated anastomosis tool may include an effector that both makes an opening in the wall of a target vessel and connects a graft vessel to the target vessel. The connection between the graft vessel and the target vessel may be compliant, and may be achieved by deploying a plurality of connectors such as staples into tissue.

SUMMARY OF THE INVENTION

The present invention relates to suturing methods and devices, including machines, needles, and methods of using them, and also for the stitches produced thereby, for suturing with reduced or minimized scarring, and that is especially useful for cosmetic-grade suturing applications and reducing suturing time.

It is an object of this invention to provide a machine constructed and configured for automatic suturing for reduced or substantially minimized scarring and reducing suturing time.

It is an object of this invention to provide methods for using a machine operable for automatic suturing for reduced or substantially minimized scarring and reducing suturing time.

Yet another object of this invention is to provide a needle designed and constructed for suturing, and more particularly for use with a machine operable for automatic suturing for reduced or substantially minimized scarring and reducing suturing time.

A further object of this invention is to provide a variety of alternative embodiments for needles designed and constructed for suturing, and more particularly for use with a device and/or a machine operable for automatic suturing for reduced or substantially minimized scarring and reducing suturing time.

Still another object of the present invention is to provide a continuous connection of loops forming a suture stitch for suturing with reduced or substantially minimized scarring and reducing suturing time.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 2 is a perspective view diagram illustrating the head of a device for suturing according to one embodiment of the invention.

FIG. 3 views A, B, C, D, E, F, G, H, I, and J illustrate a perspective view diagram of the portion of the automated machine of FIG. 1 shown in various positions of operation for a single cycle completing a stitch in suturing automated by the machine of the present invention.

FIG. 4 shows the offset subcuticular skin suturing mechanism of FIG. 1. with the tip of the helico-spiral needle in the home position (outside the skin)

FIG. 5 shows the offset subcuticular skin suturing mechanism of FIG. 1. with the tip of the helico-spiral needle in its final position after completing one skin bite.

FIG. 10 shows three perspective views 10A, 10B, and 10C each illustrating a hook in alternative embodiments for use with an automated machine for suturing of the present invention.

FIGS. 11A and 11B are tables of commercial suture materials and prior art needle references.

DETAILED DESCRIPTION

Figure 1:
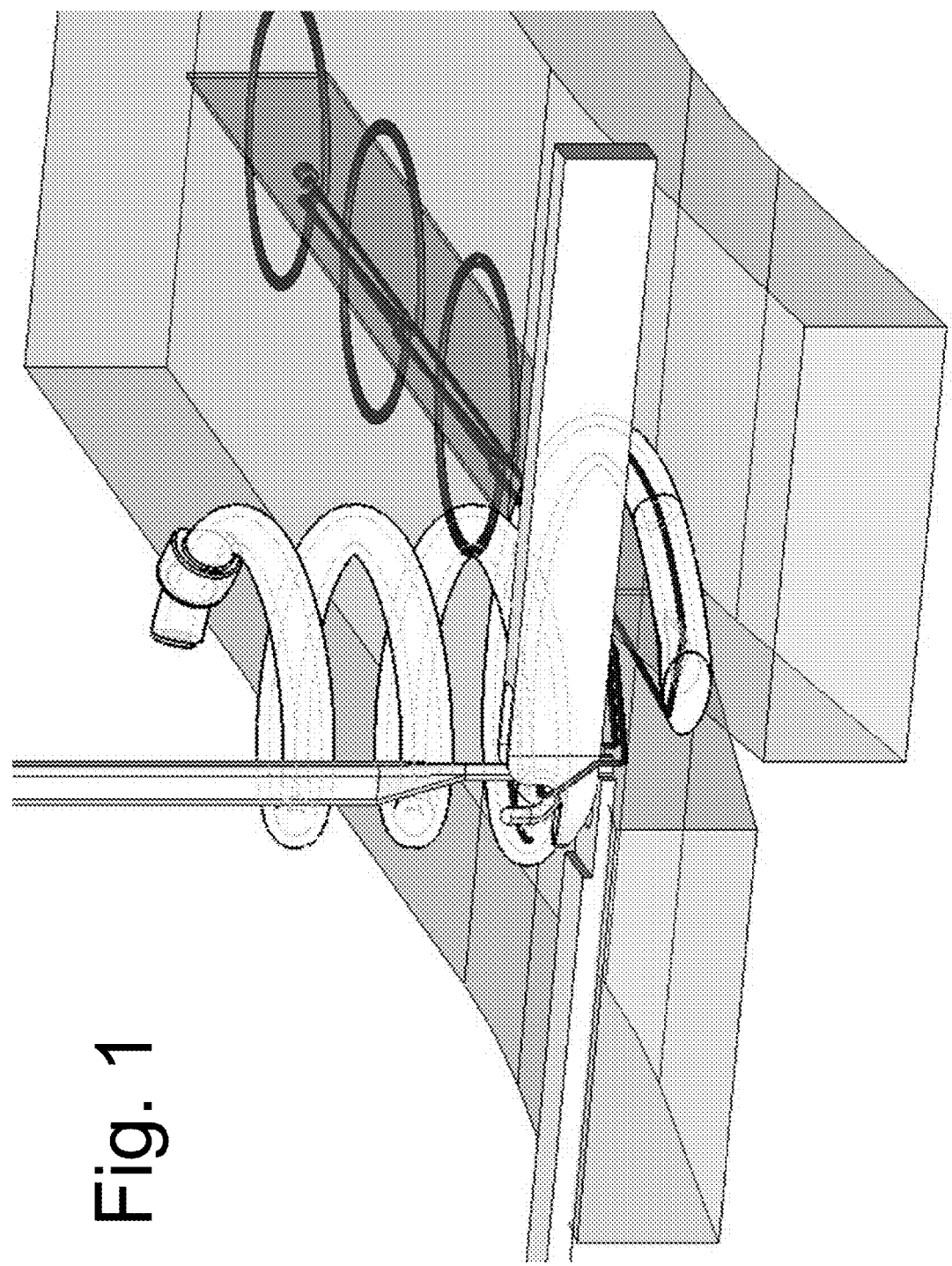
FIG. 1 is a perspective view diagram of the main components of the head of a device for suturing showing skin subcuticular suturing embodiment of the invention.

The present invention provides a device constructed and configured for automatic suturing for reduced or minimized scarring, reducing suturing time and methods for using a machine operable for automatic suturing. Additionally, the present invention provides a variety of needles, designed and constructed for suturing to minimize or eliminate scarring, reducing suturing time and more particularly for use in combination with hooks for making a continuous suture stitch with a machine operable for automatic suturing for reduced or minimized scarring, reducing suturing time.

As set forth herein, the present invention provides machines, methods and needle designs for automatic suturing with minimum scarring and reducing suturing time. Referring now to the drawings in general, the illustrations are for the purpose of describing a preferred embodiment of the invention and are not intended to limit the invention thereto.

FIG. 1 is a perspective view diagram of the main components of the head of a device for suturing showing skin subcuticular suturing embodiment of the invention.

FIG. 2 is a perspective view diagram illustrating the main components of the head of a device for suturing according to one embodiment of the invention. FIG. 3 shows a perspective view diagram illustrating a portion of the main components of the head of a device for suturing from FIG. 2 focused on the hook and needle interaction for forming continuous suture stitches according to one embodiment of the invention. The suture machine is generally referenced 10, and includes at least the following components constructed and configured in operable connection for automatically producing a stitch: a support base or housing 12, a suture thread supply (not shown) having a first end and a second end, removably (movable) mounted on the support base via a connecting cylindrical post (not shown), a substantially spiral-shaped hollow needle 18 movable rotationally between a first (home position) and second position for forming a stitch, and a hook 20 (FIG. 3) movable between a retracted 22 and an extended position (23, FIG. 3D, closer toward the needle tip than the retracted position, 22) by an automated gear device (not shown). The machine for making suture stitches automatically according to the present invention preferably includes a machine body or base for supporting or otherwise connectable to a suture thread supply, a needle constructed and configured for receiving and manipulating a first end of the suture thread supply, wherein the needle is rotationally movable so that a needle tip advances between a first and second position for adjoining at least two edges for continuously stitching them together in a substantially edge-to-edge interface without overlapping the edges, aided by a wound separator mounted on or part of the machine body 12 ahead of the suture line (the wound separator is not shown) thereby providing an automated device for making suture stitches that produce minimal scarring on tissue, organs, or skin. The wound separator is to prevent wound overlapping.

In an automated machine for suturing according to an alternative embodiment of the present invention from FIG. 2, note that the hook device mechanism may be constructed and configured to be in an angled position; preferably, the hook device mechanism is adjustable, but in any position, the hook is always configured to be in parallel to the spiral needle. However, overall components and functionality are substantially similar to the foregoing description, but the angled positioning of these components is preferred for forming a "sideways" suture using a helical needle. The angle of the spiral needle axis in relation to the surface of the tissue to be sutured is preferably adjustable between about 10 degrees and about 90 degrees, wherein 90 degrees angle is perpendicular to the wound or tissue surface where the suturing is made (i.e., the suturing zone), preferably between about 25 and about 90 degrees, and more preferably between about 45 and about 90 degrees. The application and type of suture are factors affecting the angle. The angles provide for creating hidden sutures and in the use of suturing fascia, muscles, or hollow organs, such as the intestines, wherein the skin adjoined by the sutures is substantially or perfectly flat, and without overlap, thereby minimizing scarring.

FIG. 2 is a perspective view diagram illustrating the head of a device for suturing according to one embodiment of the invention.

FIG. 3 shows a perspective view diagram illustrating a portion of an automated machine for suturing from FIG. 2 focused on the hook and needle interaction for forming continuous suture stitches according to one embodiment of the invention.

FIG. 3 views A, B, C, D, E, F, G, H, I, and J illustrate a perspective view diagram of the portion of the automated machine of FIG. 3 shown in various positions of operation for a single cycle completing a stitch in suturing automated by the machine of the present invention.

FIG. 3 shows a perspective view diagram illustrating a portion of an automated machine for suturing according to one embodiment of the invention. Furthermore, FIG. 3 views A, B, C, D, E, F, G, H, I, and J illustrate a perspective view diagram of the portion of the automated machine of FIG. 3 shown in various positions of operation for a single cycle completing a stitch in suturing automated by the machine of the present invention. By moving through this cycle automatically, a hook 20 is moved by a rotating gear (not shown) between a first retracted position (FIG. 3A) after catching a loop 34 made with the suture thread that is picked up next by a holding arm 36 that moves forward as in positions B, C, D, and E to allow the hook to move into a second extended position to release the loop and then move to catch the next loop (if any, depending on the length of the chain of stitches) illustrated in F and G positions. In this method, the suture stitch is formed of a series of interconnected loops (single stitch unit cycle is illustrated in FIG. 6; continuous series illustrated in FIGS. 7A, 7B, 7C) by the cooperation, coordination and synchronization of the needle and hook components to effectively knit the suture stitches into a connected chain that is continuous and substantially planar.

Methods for making suture stitches automatically according to the present invention include the steps of: providing a machine having a suture thread supply, a needle constructed and configured for receiving and manipulating a first end of the suture thread supply, rotationally moving the needle and thread to create a suture stitch by advancing the needle position, and adjoining at least two edges for continuously stitching them together in a substantially edge-to-edge interface, thereby making suture stitches that produce minimal scarring on tissue, organs, or skin and reducing suturing time.

In preferred methods, the step of moving the needle rotationally to create a suture stitch is automatically made, by activating the machine to move the needle to create a first rotational part of the stitch, introducing a hook in a retracted position to catch the stitch at the end of the rotational movement, reversing the direction of rotation of the needle, moving the hook to a second extended position and releasing the stitch, and extracting the needle to complete the stitch. After the needle and hook form a single stitch, or a series of connected stitches, depending upon the size of the suture area, preferably the suture thread will be cut, by scissors, or other sharp utensil. Additional cutting mechanism (not shown) can be added to the body of the machine such as a vertical blade retracted in a groove in the body of the machine. Such blade has a distal sharp flat end and blunt proximal end. The distal end is close to the stitch loop when such loop is pulled up by the hook in a retracted position inside the body of the machine. The proximal end is connected to a spring loaded button that is operated manually by the surgeon. At the end of the suture line, the surgeon can go back and forth with continuous suturing to ensure the security of the suture end. Then the surgeon pushes the button, which in return pushes the rod down to let the distal sharp flat end cut the suture material and to end the continuous line of suturing.

Figure 6:
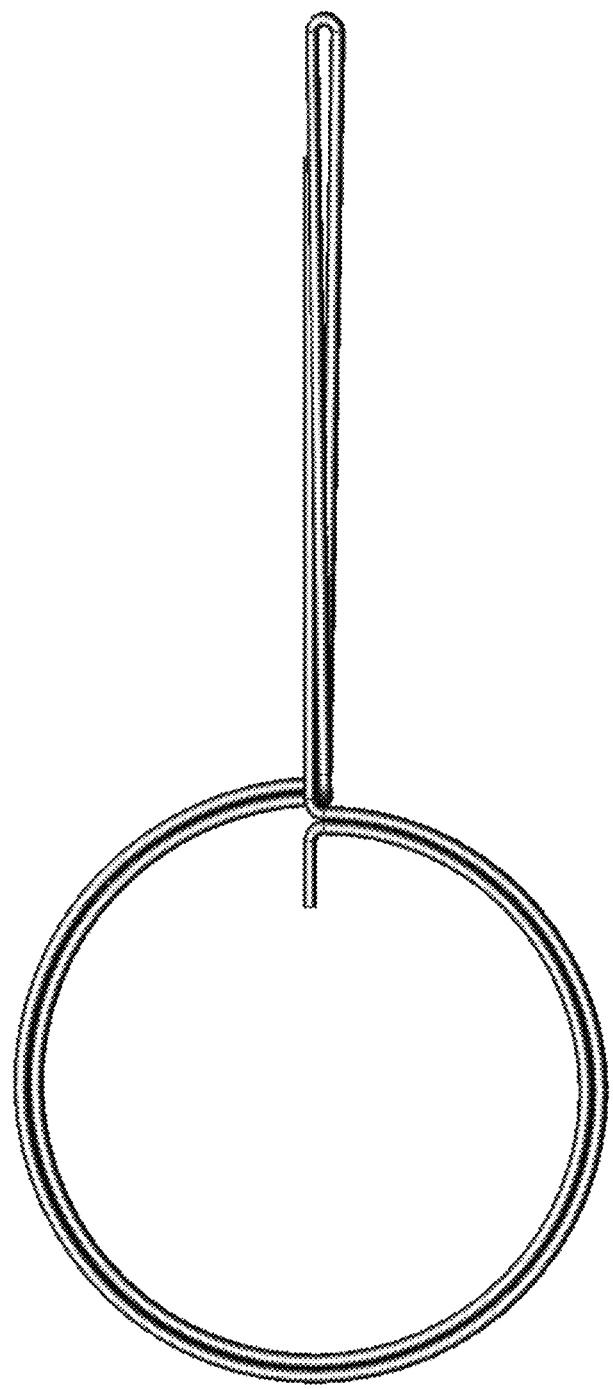
FIG. 6 shows a top view diagram illustrating a stitching pattern for a single unit cycle for making continuous suturing made by an automated machine for suturing according to one embodiment of the invention.

FIG. 6 shows a top view diagram illustrating a stitching pattern for a single unit cycle for making continuous suturing made by an automated machine for suturing according to one embodiment of the invention.

FIGS. 7 A, B, and C illustrate in perspective views three alternatives for continuous suture stitching forming chains of single unit cycles illustrated from FIG. 6.

Figures 7A, 7B, 7C:
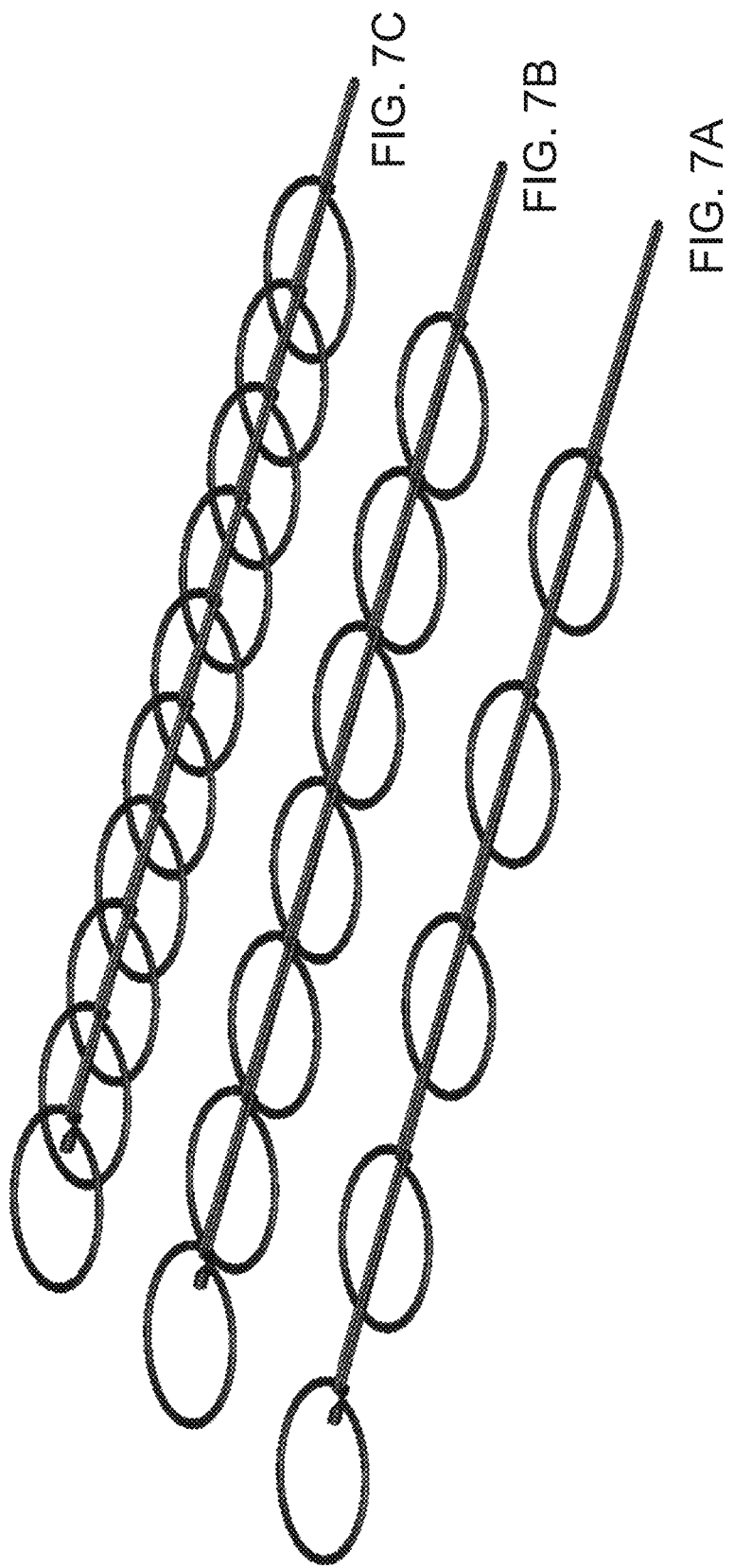
FIGS. 7 A, B, and C illustrate in perspective views three alternatives for continuous suture stitching forming chains of single unit cycles illustrated from FIG. 6

A suture stitch single unit cycle formed from the method described hereinabove is illustrated in FIG. 6, and in FIGS. 7A, 7B, and 7C, it is shown in one continuous suture stitch chain embodiment formed from a series of interconnected stitches by repeating the foregoing steps: FIG. 7A shows 5 units repeated and in a spaced apart manner so that the circular portion of the stitch unit cycle does not directly touch or is not directly juxtapositioned another stitch unit cycle; FIG. 7B shows 7 units repeated that are directly touching, i.e., the circular portion of the stitch unit cycle is formed and positioned so that it is directly or approximately directly juxtapositioned the next stitch unit cycle; FIG. 7C shows 5 stitch unit cycles wherein the circular portion of each unit cycle is overlapping with an adjacent stitch unit circular portion. The method of forming the stitch includes rotational movement of the needle via rotation of a shaft along its axis. Then parallel to the needle shaft (shown in FIG. 3), a hook catches the loop formed by the suture thread from the rotational needle movement (before or just after the needle reverses direction) and the hook pulls the loop out of the plane, as illustrated in FIG. 3 and FIG. 3 views, for forming a chain or continuous connection of a series of loops formed by the needle movement of the suture thread (single stitch unit cycle illustrated in FIG. 6; continuous suture stitching embodiments illustrated in FIGS. 7A, 7B, and 7C).

FIG. 8 shows three perspective views 8A, 8B, and 8C each illustrating a solid needle in alternative embodiments for use in suturing according to the present invention.

FIG. 9 shows three perspective views 9A (spiral needle), 9B (helico-spiral needle), and 9C (helical needle) each illustrating a hollow needle in alternative embodiments for use in suturing according to the present invention.

Figure 8C:
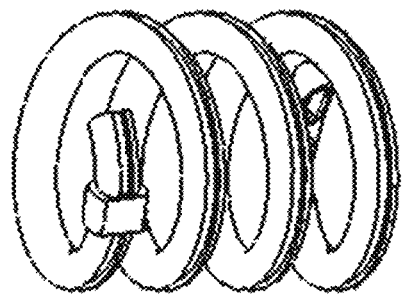
FIG. 8 shows three perspective views 8A, 8B, and 8C each illustrating a solid needle in alternative embodiments for use in suturing according to the present invention.
Figure 8B:
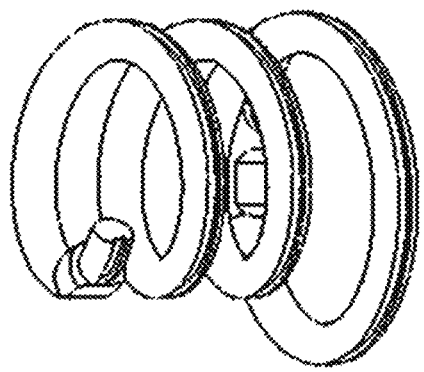
Figure 8A:
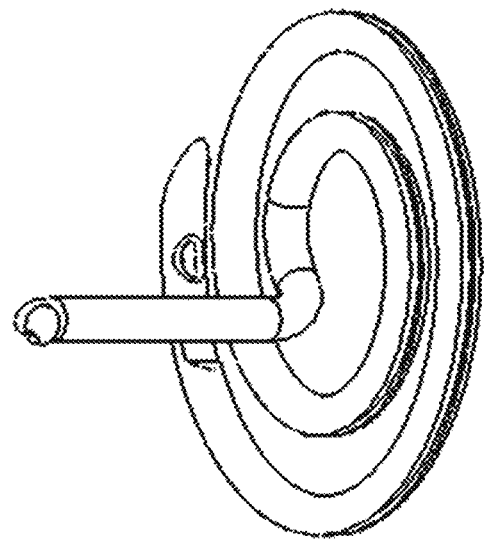
Figure 9C:
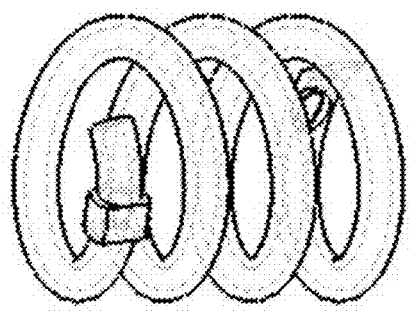
FIG. 9 shows three perspective views 9A, 9B, and 9C each illustrating a hollow needle in alternative embodiments for use in suturing according to the present invention.
Figure 9B:
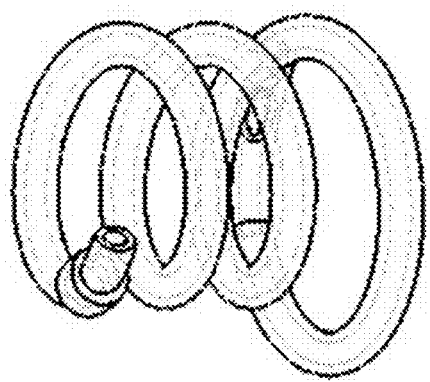
Figure 9A:
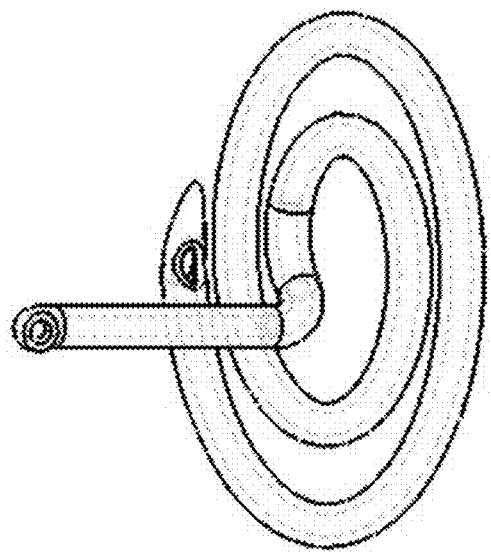
Figure 12A:
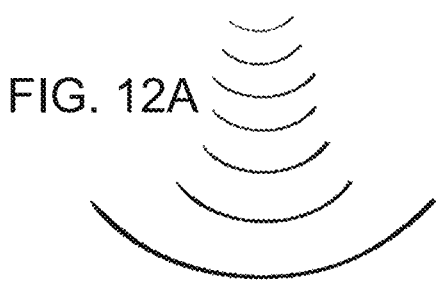
FIG. 12 is a reference table of commercial suture needle information.
Figure 12B:
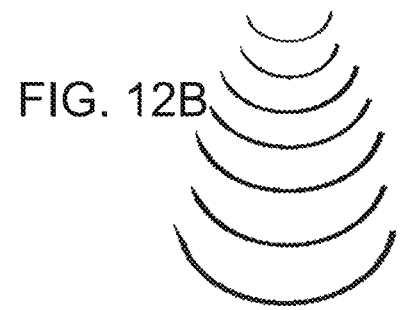
Figure 12D:
Figure 12E:
Figure 12F:

For a spiral needle as in FIG. 8A or FIG. 9A, or for the helico-spiral needle FIG. 8B or 9B, the hook is positioned preferably at 90 degree angle to the needle. For a helical needle, as illustrated in FIGS. 8C, 9C, the hook is preferably positioned at an angle with respect to the needle. For using a latch hook as in FIG. 10A, the process is not entirely dissimilar from knitting methods for creating a continuous chain of loops; however, an alternative embodiment for the machine is required (completely different from knitting machines and methods, requiring an additional catcher mechanism) when using a non-latch hook as illustrated in FIGS. 10B and 10C; in preferred embodiments, the shorter hook of FIG. 10B is used.

As illustrated in the figures, the present invention and machine and methods of using same further include a spiral-shaped suture needle for making suture stitches wherein the suture needle includes a continuously hollow needle body having a first end positioned a spaced apart distance from a second pointed, sharp end, wherein the needle body forms a spiral having at least two complete turns around a center point, wherein the second end is positioned at the outermost spiral. As shown FIG. 9 provides three perspective views 9A, 9B, and 9C each illustrating a needle in alternative embodiments for use in suturing and for use with an automated machine for suturing of the present invention. The needle body is an elongated metal cylinder that is formed and configured to be spiraled for forming the stitch for suturing in an edge-to-edge manner without substantial overlapping of the tissue, skin or organ. The important dimensions for the needle are the diameter; the height is a secondary dimension consideration. For a hollow needle, the needle tube outer diameter is preferably between about 1 mm and about 3 mm; more preferably between about 1 mm to about 2 mm. The needle spiral dimension is between about 5 mm to about 25 mm; more preferably between about 5 mm and about 15 mm. For the solid needle, the same outer diameter and the needle spiral dimension apply. The dimensions for the needle depend upon the type and size of suture thread, type and nature of tissue being connected with the suture (e.g., facial skin would require a finer needle with smaller dimensions), and other factors, including whether it is an open wound or inside the body, the size and dimensions of the device or machine, and the like. Also, the length of the needle is dependent upon the number of coils in the spiral, which is a function of the application, or the type of suture thread, type of tissue being connected with the suture, etc.

By way of example, typically used for the skin, 5/0 monocryl suture, the needle will have outer diameter of 0.36 mm and curvature of 11 mm. For fascia, muscles, and internal organs, such as intestines, larger size sutures from 4/0 up to about #2 would require much larger needle and curvature. Smaller sizes would be used for microsurgery, and eye surgery.

In one embodiment, preferably the second pointed sharp end is angled to expose an ovular opening of the needle body. Such opening is preferred to have smooth rounded edges to allow the suture material to slide easily with minimal friction especially if used with the hollow helico-spiral needle. Preferably the suture needle further includes an opening spaced apart from the second pointed sharp end of the needle for forming the suture stitch and to allow the suture thread to exit at the side or edge of the tissue. A latch needle or spring needle or hybrid of both may be used with machines of the present invention. Steps for methods of using these needles with or without the machines of the present invention include: inserting the needle at the point or location for the first suture stitch; catching the suture stitch with the hook; pulling out the needle by reversing its rotation; the hook releasing the loop; holding the loop by the catcher, hooking the next loop by the hook and pulling it through the previous suture stitch loop (illustrated by the positions of machine components in FIG. 3A-G) to form a substantially parallel series of continuous loops along the suture tissue line. In a significant difference from knitting known in the prior art, the stitching of loops for forming the sutures of the present invention are formed in a single flat line and only connected on a single side of the loop of the stitches, as illustrated in FIG. 6.

FIG. 6 illustrates a view showing single side loops that are connected.

The bottom loop goes through the opposing side loop for interconnecting and closing the wound from both sides. These illustrations in the figures provide step by step methods for making the suture according to the present invention, and also show the device and/or machine component positioning and configuration at each step. Depending upon where the next stitch entry is made determines the pattern and closure for the suture stitch; three embodiments of suture stitch chains are illustrated, from spaced apart non-interlacing or overlapping loops; to another view showing adjacent loops that are juxtapositioned but not overlapping; and a third view showing overlapping or interlacing loops or stitches. In each example embodiment, a perspective view is shown.

In preferred embodiments, it is better to stretch the stitch longer, i.e., to make the circular loops stretched (each loop circle is stretched longer); it is helpful for the purposes of this detailed description of the invention to consider each loop as a unit cell. Depending on a link from each end of the unit cell, determines how tightly each unit cell is positioned. Each entry into the skin/tissue/organ is more distantly spaced apart.

FIGS. 8C, 9C show a perspective views for one of the suture needle configurations, although it is not preferred, since there are too many coils, which makes more friction for the suture inside. It would be preferred to place the suture outside that needle when it is used.

FIGS. 8A, 9A show another compact view of a needle embodiment of the present invention; however, it is likewise not the preferred embodiment, because when the needle starts to rotate, there is still a need to squeeze the wound to press together the wound edges to be stitched. Position of hook would be straight for A, which is acceptable, but not preferred.

FIGS. 8B, 9B are preferred needle types (solid more preferred than hollow) and illustrates a hybrid between 9A and 9B because some part of the spiral shape with helical, but not completely conical; it is instead from spiral to helical, and is the preferred needle embodiment—the helical-spiral (or helico-spiral) hybrid needle.

A compact device embodiment is preferred, wherein the last circle of the needle component is spiral, with two helical and last one on bottom is spiraled out wider; the latch needle is positioned to be operable in a vertical up and down movement. In methods preferred and illustrated in this figure, steps are included to catch the loop from both sides so that a catch makes a loop of the suture on both sides; on one cycle there is a catching mechanism to catch from left side; then a step to pull the latch mechanism up; then a step to retract the spiral needle; then the catcher and the latch needle (hook) work together to catch the loop on the other side, so it goes through first loop and pulls through the second loop, and each time comes from one side of the wound. One time it is at an acute angle; one time straight.

By way of preferred embodiment for an example or prototype of the present invention, a solid needle is provided with helical-spiral shape. While a hollow needle is possible, at the time of the invention example, it is practically easier to make a device according to the present invention with a solid needle. One reason is that it is easier to pull out the suture to make the wound tighter; another is that it is also easier to use a solid needle in combination with a spring-based or lever-based tensioner or tension-providing mechanism. A commercial reason for preferring a solid needle instead of a hollow needle configuration is that the hollow needle is more expensive to produce. Also, there is some difficulty threading it, and in operation, there is additional friction and tension in the needle since the suture thread passes through and contacts the needle's internal surfaces in this hollow needle configuration. For these reasons, in the preferred embodiments at the time of the present invention, non-hollow needle components are used in prototype experimentation.

Figure 3G:
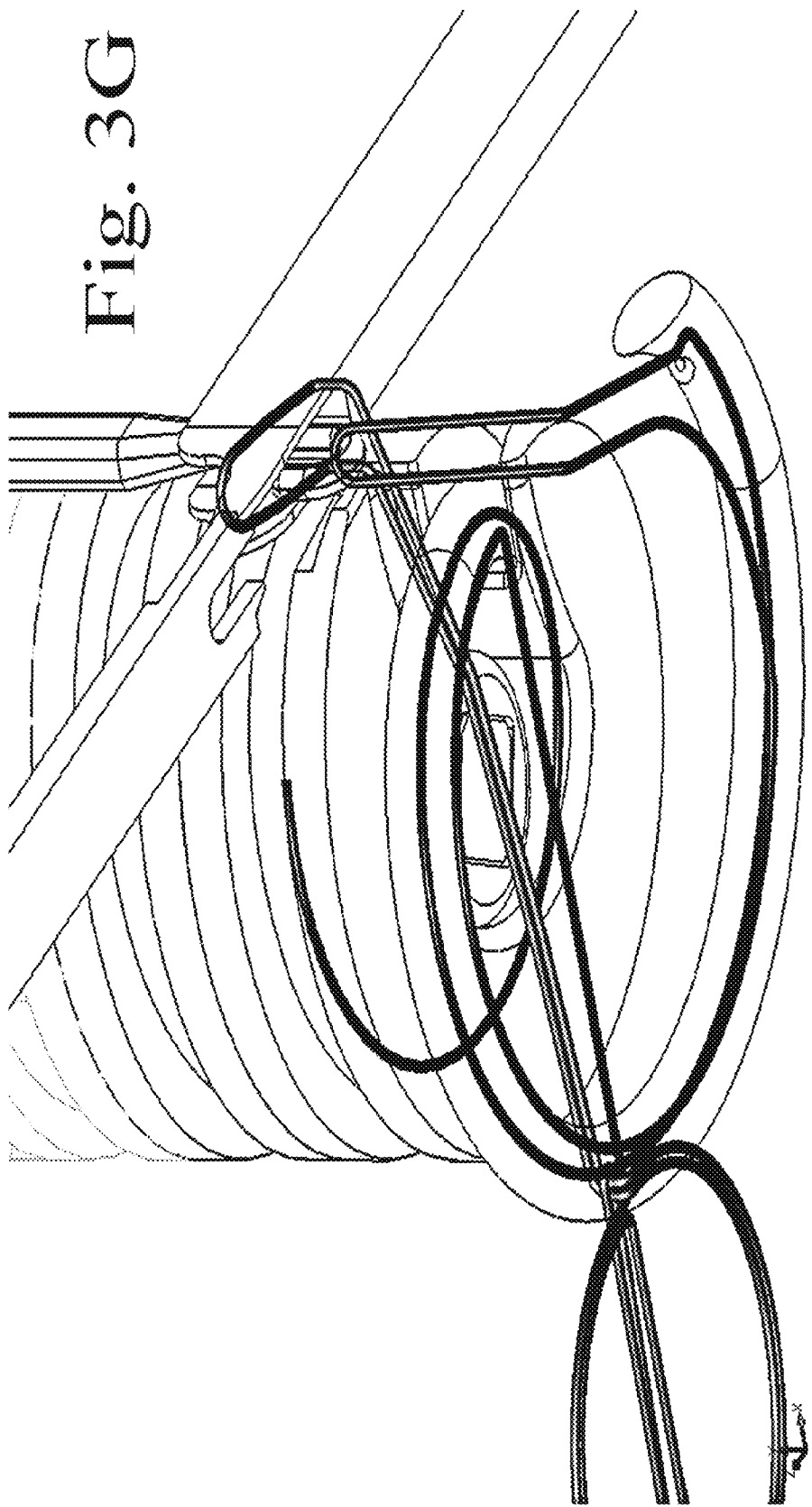
FIG. 3 shows a perspective view diagram illustrating a portion of an automated machine for suturing from FIG. 1 focused on the hook and needle interaction for forming continuous suture stitches according to one embodiment of the invention.
Figure 3I:
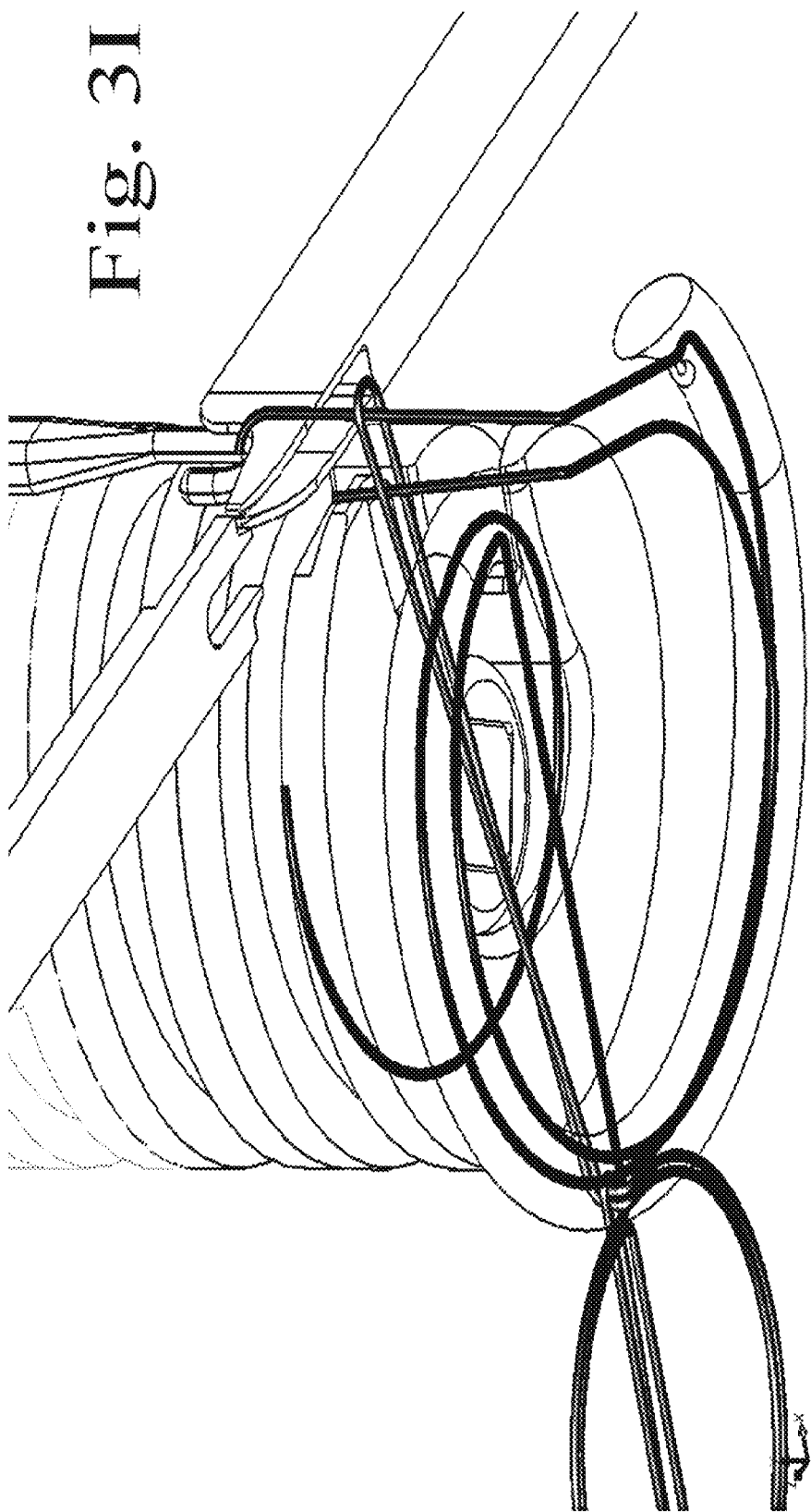

Note that in FIG. 3 and the various FIGS. 3A-3J, all illustrations show the continuous suture stitch beginning with a knot. Now regarding the illustrations of FIG. 3 and FIGS. 3A-3J, starting from position zero in the formation of a single suture stitch unit cycle the steps are as follows:

Position zero. The hook is positioned up; the catcher has a multiplicity of positions, preferably with 3 positions: home, catch, and push positions that are illustrated in the various figures. The catcher hooks the loop when the catcher is positioned in a second position, and it is also hooked on the loop at that time. Two alternatives are considered in prototype versions of the embodiments of the present invention that use a vertical needle: 1) go through the loop exactly; and/or 2) go through the loop and past it. If the first alternative is used, then the methods for making sutures according to and with the device and machine according to the present invention provide for the following steps: pushing the suture to that position to make a space for the hook to go exactly through the loop. In this step, it is very important for safety that there be adequate space for the hook to move exactly through the loop, otherwise it is possible to lose at least one stitch in the next or following step(s).

The suture goes through the hole in the helical spiral hybrid needle and through the tube (in the case of a hollow needle embodiment) up to the spool. In a prototype version according to one embodiment of the present invention, the suture goes through needle and through body on the right side for pulling the suture with an additional mechanism. Again, for commercial application, the solid or non-hollow needle is preferred over use of application of hollow needle configuration since the hollow needle is expensive to produce, there is some difficulty threading it, and there is additional friction and tension in the needle during its use in methods of the present invention, since the suture thread passes through and contacts the needle's internal surfaces in this hollow needle configuration. For these reasons, in the preferred embodiments at the time of the present invention, non-hollow needle components are used in prototype experimentation.

Again, referring to the method steps illustrated in FIG. 3 and FIGS. 3A-3J. Once the final position zero is returned to, a single unit cell or unit cycle is completed.

Position 1. For the next bite or next step in forming a continuous suture stitch chain as illustrate in the Figures: shift the entire mechanism forward. The way the mechanism shifts and how the suture goes from the helico-spiral needle and pulls the loop held by the vertical hook. If additional tension or pull is provided on the loop, it makes the wound tighter.

Position 2. First bite or needle entry into the wound. Hole in needle near tip or sharp end to show how the suture thread or suture material exits the needle and goes to tensioning device.

Position 3. Rotation is 45 degrees from p1 to p2. This is now 360 degrees rotation. Radius of needle is smaller than the first rotation from the tip of the needle b/c spiral.

One suture all the way up; 2d goes through the wound.

The figures also show stitched loops with reference to left side of wound; right side of wound.

Next the final position of the helico-spiral needle before catching the suture is shown.

Catcher pushes the loop from the hook. The vertical needle hook is lower; catcher pushes the loop & holds it in a position. At that point the hook starts moving down exactly through the loop because it's held in 2 directions horizontal and vertical to assure that one loop goes through another; this is critical in the methods of the present invention.

After that hook goes through the lower position, close to the helico-spiral needle to ensure that the hook passes through the space between the suture and the helico-spiral needle to be ready to catch the loop.

At the bite, it is from the front side of the loop. When the needle rotates, diagram 3D, the needle is positioned below the loop. The helico-spiral needle rotates backwards 45 degrees and the vertical hook captures the next suture, and then pulls out the next loop. The prior loop is inside of the helico-spiral needle.

The new loop is pulled through the prior loop. Next the vertical hook is positioned up; pusher retracts. Before retracting catcher to right, the vertical hook is pulled up. Then retract the catcher. The chain is now made forming the circular portion for the continuous suture stitch. Next the catcher moves or is pushed to catch the next loop (the new loop).

Then go to or return to position zero (0).

The method steps are focused on one bite at a time for these steps in the exploded partial views of the FIGS. 3, 3A-3J.

Note that these diagrams are all indicated as being oriented to the wound without angle. It could be vertical for skin. If muscles or other organs, it may be 45 degree angle. In the skin, you take bites parallel to skin. For muscles, fascia or internal organs it may be preferable to angle the entire the machine, or change the angle of the base of the machine body in a way to serve the function of suturing the target tissue.

As will be appreciated there are a variety of different suture materials may be used; these may range from 10/0 smallest to #2. Refer to the tables 1 and 2 for suture material and for needles used commercially. Regarding preferred size of needle, it depends on tissue type. Regarding size of the device, overall width is preferably less than one inch, which is about the size of a basic suture width. Commercial device would be preferably about ½ inch. Note that the most important dimension relating to the present invention is the diameter of the helico-spiral needle spiral.

In other embodiments of the machines of the present invention, the machines are preloaded with a suture thread that is knotted at its first end so that at the first stitch, the knot catches inside the tissue to be stitched. Overall dimensions of the machine for automated suturing, particularly for disposable machines intended for single use application provide for a machine height less than about one inch. A quick connect is preferred to attach the machine housing and functional components to a handle and motor shaft. Advantageously, the methods of the present invention provide for better cooptation of the wound; and this reduces the chance of infection. If used for hollow organs, intestines, it will minimize leakage. Also note that it facilitates surgical suturing and minimizes the time of suturing. Speed is very important. The methods of the present invention are at least about twice as fast as manual suturing methods.

In other embodiments of the present invention, preferably a guard is provided to maintain the tissue to be sutured in a substantially edge-abutting position equal on both sides of the needle and hook region of the machine; also preferably a separator at the front of the stitching area is provided, such as by way of example and not limitation, a separator comprising a vertical plunger device or mechanism.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. Applications to close skin, muscles, fascia, hollow organs like intestines, bladder, etc. The device can be modified with an extended shaft such that it can be used through a laparoscope in laparoscopic and robotic surgery. Note also that the machine may be programmed by microprocessor, program, controlled by circuit board, timing controls and set of gears and micro servos to coordinate all the motions to be fully automated and programmable.

Also, a footing mechanism with roller can be added to the base of the device where it comes in contact with the sutured tissue so as to advance the machine in synchronized motion with the helico-spiral needle. The roller mechanism can advance the device in relation to the sutured tissue at predetermined speed.

The base (footing) of the body of the machine (device) can be modified to allow the device to perform subcuticular skin suturing (inserting the suture beneath the outer layer of the skin, parallel to the skin surface). This is a standard surgical technique that is done, prior to this art, manually by the surgeon to achieve cosmetic healing with minimal scarring. It is a tedious process and time consuming. This invention makes this process speedy and consistently accurate.

To achieve the above-mentioned objectives, the footing (not shown) of the device that comes in contact with the skin surface is offset. Thus, the skin surfaces of the cut are offset, FIG. 4; with one side 52 higher than the other side 53. Distance 50 in FIG. 4 represents this offset, which is equal to pitch of the helico-spiral needle, that is, the distance 51 (the distance between the coils of the helico-spiral needle).

As a result of the offsetting of the foot of the device, the skin surface is also offset with equal distance as the device-footing offset. In an example embodiment, this distance is about 2 mm, which is the average thickness of the outer layer of the skin below which it is desirable to insert the subcuticular skin sutures to achieve cosmetic result with minimal scarring. When the helico-spiral needle starts its turn stitch cycle, it first enters the subcutis on the edge 52 (FIG. 4) on the side of the wound that is higher, sideways tangential (parallel) with the skin surface and preferably perpendicular to the wound edge. In cases where the edge is not planar, the surgeon can make the appropriate entry such that the stitch will bring the tissue edges in proper apposition. The needle continues its rotation beyond the 180 degrees, going lower while rotating until it exits the first side 52 and enters the skin edge on the lower side of the wound 53 FIG. 5.

The needle completes a 360 degree rotation, exiting the left edge of the wound about 1 mm below the depth of the entry point, and continues turning about 45 degrees to allow the vertical hook 22 FIG. 5 to pick the suture loop up. The helico-spiral needle then reverses direction 405 degrees backwards to return to its home base in the device housing, thus completing one stitch cycle. Thus, the helico-spiral needle rotates at least about one and one-eighth turns. The whole device advances forward to start another stitch cycle, the skin edges that have been sutured come together in apposition with edge to edge adaptation and surface to surface configuration that provides for cosmetically acceptable scarring as healing can occur without skin edges overlapping and the cutis is not disturbed by sutures.

To further clarify the orientation of the device in relation to the wound, we consider the front of the wound, that area of the skin that has not been sutured yet in front of the advancing device and the back of the wound is that area of the skin that has been sutured.

The footing of the device is flat (on the same plane) on both sides behind the area where the slanted surface ends and meets the flat surface 54 FIG. 5. Thus, the skin surface that has already been sutured and underneath this back part of the device housing, is on the same plane without any offsetting, hence without skin edge overlap.

Another advantage of the subcuticular suturing technique is that the suture material is hidden underneath the skin, thus leaving no skin marks, compared to the standard skin stapling technique or other methods of suturing whereas the suture material is exposed outside the skin. The subcuticular suture material that is proposed to be used by the device is absorbable by the body in few weeks (see Ethicon suture table 1) thus there is no need to remove the suture later on. An example of such suture material is the mono-filament suture called Monocryl 5/0 (Ethicon trademark).

Also, keeping the suture material underneath the skin does minimize the chances of wound infection and it also eliminates the pain associated with removing the suture 7-10 days later on (such is the case when using the standard method of skin suturing). The patient also feels much less pain associated with subcuticular suturing compared with the standard exposed sutures.

Note that the present invention provides for continuous suturing; however, the device does not move at constant speed when in use; so then preferred methods of the present invention provide for a visual indication showing when to move the device, and/or in automated versions for a machine, the machine is preferably programmed to move only when the needle is out of the tissue.

By way of example and not limitation, it is considered within the scope of the present invention that the machines, methods, and needles may be adapted for stitching non-biologic material, or for non-medical purposes, such as stitching leather, artificial leather, etc. Thus, the device of the present invention can use different types of suturing materials to meet different needs. Also possible use of the device in different industries, such as by way of example and not limitation, veterinary medicine, textiles, automotive, industrial, and other markets. All modifications and improvements have been deleted herein for the sake of conciseness and readability but are properly within the scope of the present invention.

The invention claimed is:

1. A device for making continuous suture stitches comprising:
   a handle with a front end and a device head removably attached to the handle at the front end;
   the handle comprising a housing enclosing a power source for the device head and a means for attachment to the device head;
   the device head comprising:
   a suture thread supply;
   a needle rotationally movable, operable for moving the thread through a tissue;
   a hook operable for hooking and lifting the thread in automatic coordination with the needle;
   a catcher operable for moving the thread into and out of the hook in automatic coordination with the hook; and
   a housing operable for maintaining the suture thread supply, the needle, the hook and the catcher in position and to attach the device head to the handle at the front end;
   thereby providing a device for making continuous suture stitches for adjoining a first edge and a second edge of a tissue in an edge-to-edge interface.

2. The device of claim 1, wherein the needle is a helical, spiral, or helico-spiral needle with a pitch.

3. The device of claim 1, wherein the needle is operable for rotating between a first and second position for introducing the thread into the first edge and the second edge of a tissue.

4. The device of claim 1, further comprising a wound separator to prevent wound overlapping.

5. The device of claim 1, further comprising an offset footing positioned for providing an offset between a first and second edge of a cut; and wherein the offset is equal to the pitch of the needle.

6. The device of claim 5, wherein the offset is greater than the thickness of the outer layer of the skin.

7. The device of claim 5, wherein the needle and the footing are operable to exit the needle from a wound at about 1 mm below the depth of the entry point of the needle.

8. The device of claim 5, wherein the needle and the footing are operable to maintain the needle in the subcutis throughout the revolution of the needle.

9. The device of claim 5, wherein the offset footing further comprises a roller.

10. A device for making continuous suture stitches comprising:
a handle and a device head removably attached to the handle;
the device head comprising:
a suture thread supply;
a needle rotationally movable, operable for moving the thread through a tissue;
a hook operable for hooking and lifting the thread in automatic coordination with the needle;
a catcher operable for moving the thread into and out of the hook in automatic coordination with the hook; and
thereby providing a device for making continuous suture stitches.

11. The device of claim 10, wherein the needle is helical, spiral, or helico-spiral shaped.

12. A device for making continuous suture stitches comprising:
a needle constructed and configured for receiving a suture thread;
a hook constructed and configured for translational movement in automatic cooperation with the needle for manipulating the suture thread; and
a catcher comprising a push and a catch arm in automatic coordination with the hook;
thereby providing a device for making continuous suture stitches.

13. The device of claim 12, wherein the needle is helical, spiral, or helico-spiral shaped.

14. The device of claim 12, wherein the needle rotates about 405 degrees to create a stitch.

15. The device of claim 12, wherein the needle has an axis of rotation and the hook is positioned parallel to the axis of rotation and configured for translational movement between a retracted and extended position for receiving and releasing the suture thread in automatic coordination with the needle.

16. The device of claim 12, wherein the catcher is positioned perpendicular to the hook and comprises a push and a catch arm configured for translational movement for pushing and catching the thread in automatic coordination with the hook.

17. The device of claim 12 wherein the device further comprises a cutting mechanism for cutting the thread.

18. The device of claim 12, wherein the device further comprises a guard to maintain the edge-to-edge interface.

19. The device of claim 12 wherein the needle and the hook are adjustable to be configured in an angled position relative to a surface being stitched.

20. The device of claim 12, wherein the needle is solid or hollow.

* * * * *